US012661451B2

(12) United States Patent
Daniel

(10) Patent No.: US 12,661,451 B2
(45) Date of Patent: *Jun. 23, 2026

(54) SINGLE DOSE MEDICAMENT DELIVERY DEVICE

(71) Applicant: SHL Medical AG, Zug (CH)

(72) Inventor: Mattias Daniel, Täby (SE)

(73) Assignee: SHL Medical AG, Zug (CH)

( * ) Notice: Subject to any disclaimer, the term of this patent is extended or adjusted under 35 U.S.C. 154(b) by 820 days.

This patent is subject to a terminal disclaimer.

(21) Appl. No.: 18/062,726

(22) Filed: Dec. 7, 2022

(65) Prior Publication Data

US 2023/0107287 A1     Apr. 6, 2023

Related U.S. Application Data

(63) Continuation of application No. 17/062,718, filed on Oct. 5, 2020, now Pat. No. 11,872,378, which is a
(Continued)

(30) Foreign Application Priority Data

Aug. 19, 2015     (SE) .................................... 1551080-3

(51) Int. Cl.
*A61M 5/31*          (2006.01)
*A61M 5/20*          (2006.01)
(Continued)

(52) U.S. Cl.
CPC ........ *A61M 5/3146* (2013.01); *A61M 5/2033* (2013.01); *A61M 5/31501* (2013.01);
(Continued)

(58) Field of Classification Search
CPC .............. A61M 5/3146; A61M 5/2033; A61M 5/31501; A61M 5/31553; A61M 5/31563;
(Continued)

(56) References Cited

U.S. PATENT DOCUMENTS 5,843,036 A * 12/1998 Olive .................. A61M 5/2033
604/134
2004/0236284 A1* 11/2004 Hoste .................... A61M 5/326
604/198
(Continued)

FOREIGN PATENT DOCUMENTS

CN          101903059 B      6/2013
CN          103945881 A      7/2014
(Continued)

OTHER PUBLICATIONS

International Search Report and Written Opinion for Int. App. No. PCT/EP2016/066503, completed Sep. 29, 2016.*.

*Primary Examiner* — Lauren P Farrar
(74) *Attorney, Agent, or Firm* — McDonnell Boehnen Hulbert & Berghoff LLP

(57) ABSTRACT

A medicament delivery device configured to provide a variable single dose of medicament is disclosed. The medicament delivery device includes a main body and a syringe arranged in the main body, wherein the syringe comprises a medicament. The medicament delivery device further includes a removable cap and a plunger rod operatively arranged to eject the medicament through a delivery member i.e. an injection needle attached to the syringe. Still further, the medicament delivery device includes a tubular member coupled to the plunger rod. The tubular member is configured to rotate during removing of the removable cap, and the rotation releases the plunger rod thereby allowing the plunger rod to travel a predetermined distance so as to prime the medicament delivery device.

20 Claims, 18 Drawing Sheets

Related U.S. Application Data continuation of application No. 15/748,974, filed as application No. PCT/EP2016/066503 on Jul. 12, 2016, now Pat. No. 10,857,300.

(51) Int. Cl.
　　*A61M 5/315*　　　(2006.01)
　　*A61M 5/32*　　　(2006.01)

(52) U.S. Cl.
　　CPC . *A61M 2005/2013* (2013.01); *A61M 5/31553*
　　　(2013.01); *A61M 5/31563* (2013.01); *A61M*
　　　*5/3202* (2013.01); *A61M 2005/3217* (2013.01);
　　　*A61M 5/326* (2013.01); *A61M 2005/3267*
　　　(2013.01); *A61M 2205/702* (2013.01)

(58) Field of Classification Search
　　CPC ................ A61M 5/3202; A61M 5/326; A61M
　　　2005/2013; A61M 2005/3217; A61M
　　　2005/3267; A61M 2205/702
　　See application file for complete search history.

(56) References Cited

U.S. PATENT DOCUMENTS

| | | | |
|---|---|---|---|
| 2005/0203466 A1* | 9/2005 | Hommann ............ | A61M 5/326 |
| | | | 604/240 |
| 2013/0035644 A1 | 2/2013 | Giambalttista et al. | |
| 2013/0144218 A1 | 6/2013 | Daniel | |
| 2013/0197479 A1 | 8/2013 | Butler et al. | |
| 2014/0025013 A1 | 1/2014 | Dowds | |
| 2014/0228769 A1 | 8/2014 | Karlsson et al. | |
| 2014/0343507 A1 | 11/2014 | Karlsson et al. | |
| 2015/0202380 A1 | 7/2015 | Harms et al. | |
| 2018/0264196 A1 | 9/2018 | Fabien | |

FOREIGN PATENT DOCUMENTS

| | | |
|---|---|---|
| CN | 104470564 A | 3/2015 |
| CN | 103732276 B | 11/2015 |
| CN | 102917738 B | 1/2016 |
| TW | 201116314 A | 5/2011 |
| TW | 201231113 A | 8/2012 |
| TW | 201330890 A | 8/2013 |
| TW | 201402169 A | 1/2014 |
| WO | 2003053499 A1 | 7/2003 |
| WO | 2005009515 A1 | 2/2005 |
| WO | 2007131013 A1 | 11/2007 |
| WO | 2007131025 A1 | 11/2007 |
| WO | 2009114542 A1 | 9/2009 |
| WO | 2009137486 A1 | 11/2009 |
| WO | 2010017650 A1 | 2/2010 |
| WO | 2010023481 A1 | 3/2010 |
| WO | 2010149214 A1 | 12/2010 |
| WO | 2011003980 A1 | 1/2011 |
| WO | 2011039231 A1 | 4/2011 |
| WO | 2011048223 A1 | 4/2011 |
| WO | 2012/122643 A1 | 9/2012 |
| WO | 2012163890 A1 | 12/2012 |
| WO | 2013016832 A1 | 2/2013 |
| WO | 2013/048310 A1 | 4/2013 |
| WO | 2013092670 A1 | 6/2013 |
| WO | 2013156516 A1 | 10/2013 |
| WO | 2013169800 A1 | 11/2013 |
| WO | 2014/095424 A1 | 6/2014 |
| WO | 2014/096396 A1 | 6/2014 |
| WO | 2014/166914 A1 | 10/2014 |
| WO | 2015087090 A2 | 6/2015 |
| WO | 2015166286 A2 | 11/2015 |
| WO | 2017029032 A1 | 2/2017 |
| WO | 2019224784 A1 | 11/2019 |

* cited by examiner

100

120

211

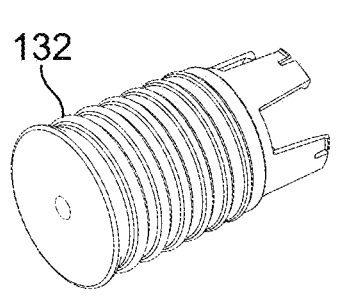
FIG. 28A
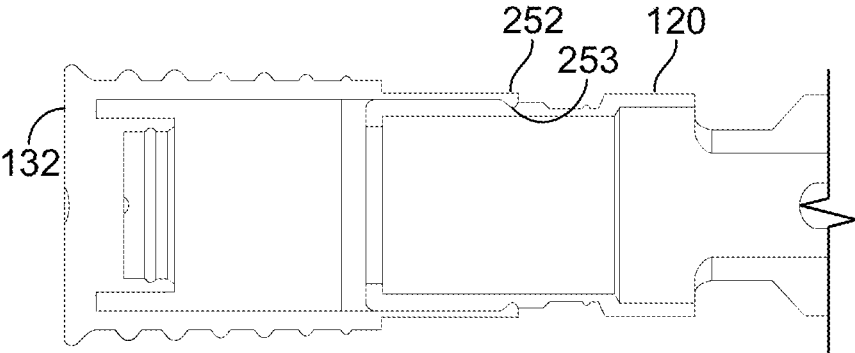
FIG. 28B
FIG. 29
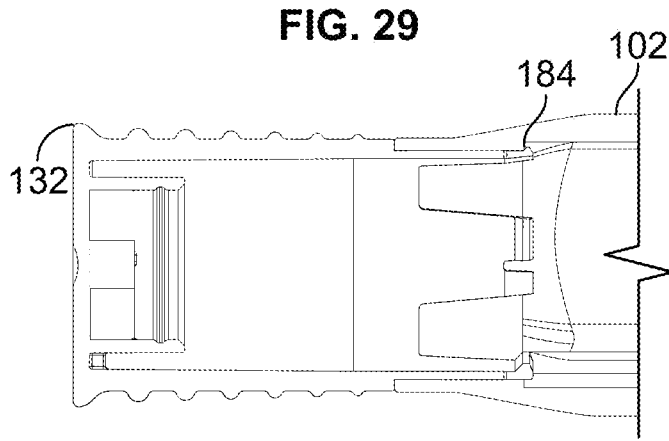
FIG. 30
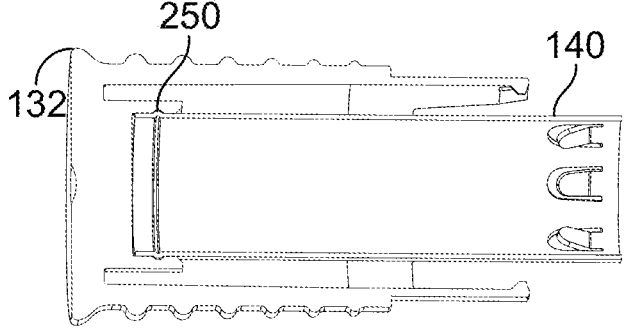
FIG. 31

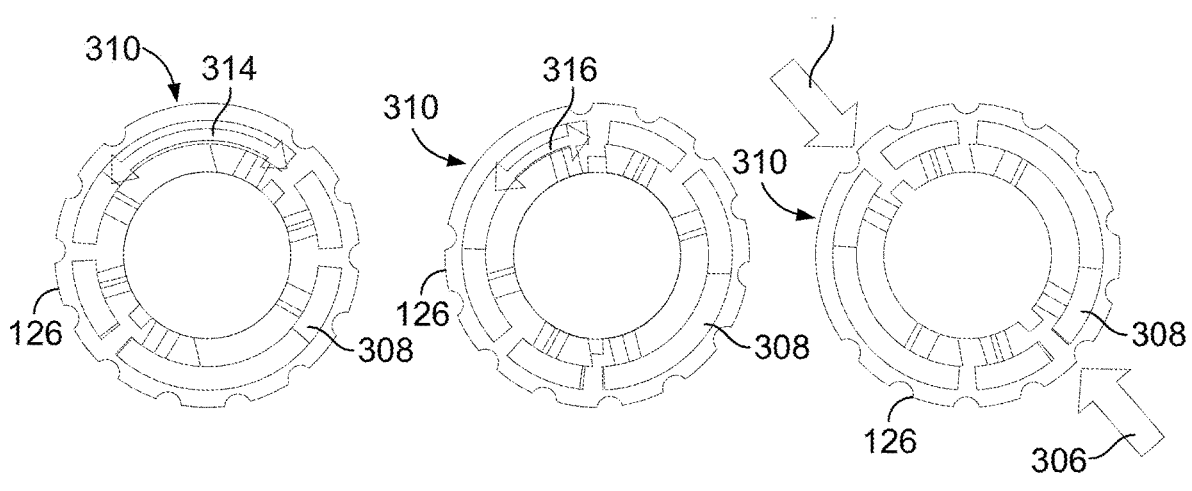
FIG. 36A          FIG. 36B          FIG. 36C
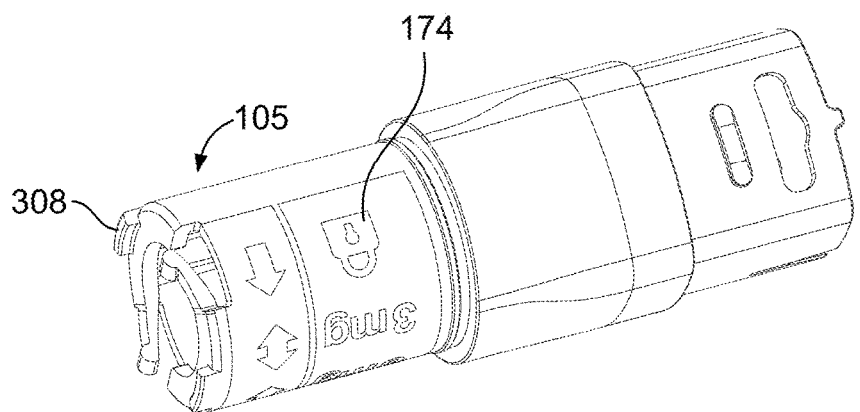
FIG. 37
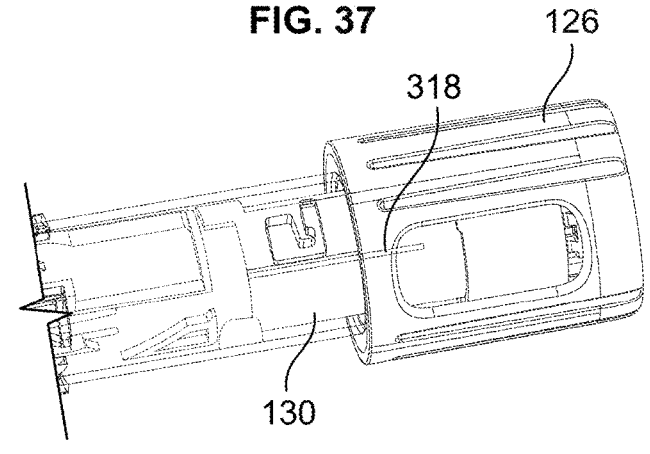
FIG. 38

SINGLE DOSE MEDICAMENT DELIVERY DEVICE

CROSS REFERENCE TO RELATED APPLICATIONS

The present application is a continuation of U.S. patent application Ser. No. 17/062,718 filed Oct. 5, 2020, which is a continuation of U.S. patent application Ser. No. 15/748, 974 filed Jan. 30, 2018, which is a U.S. National Phase Application pursuant to 35 U.S.C. § 371 of International Application No. PCT/EP2016/066503 filed Jul. 12, 2016, which claims priority to Swedish Patent Application No. 1551080-3 filed Aug. 19, 2015. The entire disclosure contents of these applications are herewith incorporated by reference into the present application.

TECHNICAL FIELD

This present disclosure relates to relates to medicament delivery devices such as automatic injection devices that may be primed.

BACKGROUND

Unless otherwise indicated herein, the materials described in this section are not prior art to the claims in this application and are not admitted to be prior art by inclusion in this section.

In some situations, it is desirable for patients to be able to administer drugs and medicament by themselves, e.g., without the need for trained medical staff to administer the drugs. There are a number of different existing delivery devices with varying degrees of automatic functions. There are however a number of considerations to take into account for medicament delivery devices that are to be used by non-trained persons in view of safety (e.g., for the user and others that may come in contact with the device) as well as in view of handling and operation.

In an example, for safety reasons many devices have been arranged with a cover or other protection means that is manually or automatically activated in order to, for example, protect persons from an injection delivery member i.e. injection needle, both before and after use of the medicament delivery device.

For some types of medicament enclosures and treatment schemes there is a need to deliver a precise dose, which may be less than the total amount in the enclosure. Further, in some circumstances, it is also desirable to perform a priming procedure of the device and/or delivery member i.e. injection needle before dispensing the medicament. Many devices are provided with medicament enclosures such as cartridges, ampoules or syringes containing medicament in liquid form. When filling these containers with liquid, a small amount of air is often entrapped in the container and this air should be removed before delivery. Some devices are of multi-chamber type where one component is powder and the other is liquid or two liquids or more liquids and powder chambers.

SUMMARY

A medicament delivery device configured to administer a variable single dose of medicament is provided. In an example embodiment, the medicament delivery device includes a main body and a syringe arranged in the main body, wherein the syringe comprises a medicament. Further, the medicament delivery device includes a delivery member shield unit slidably arranged in the main body, a removable cap releasably coupled to the delivery member shield unit, and a plunger rod operatively arranged to eject the medicament through a delivery member e.g. an injection needle attached to the syringe. Still further, the medicament delivery device includes a tubular member arranged inside the delivery member shield unit, wherein the tubular member is coupled to the plunger rod, and wherein the tubular member comprises a track. The delivery member shield unit comprises a pin configured to interact with the track of the tubular member. During removing of the removable cap, the pin on the delivery member shield unit travels in the track on the tubular member so as to cause rotation of the tubular member, wherein the rotation releases the plunger rod thereby allowing the plunger rod to travel a predetermined distance so as to prime the medicament delivery device.

In another example embodiment, the medicament delivery device includes a main body and a syringe arranged in the main body, wherein the syringe comprises a medicament. The medicament delivery device further includes a removable cap and a plunger rod operatively arranged to eject the medicament through a delivery member e.g. an injection needle attached to the syringe. Still further, the medicament delivery device includes a tubular member coupled to the plunger rod. The tubular member is configured to rotate during removing of the removable cap, and the rotation releases the plunger rod thereby allowing the plunger rod to travel a predetermined distance so as to prime the medicament delivery device.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary embodiments are described herein with reference to the drawings, in which:

FIGS. 28*a-b* depict a perspective view of a removable cap of the medicament delivery device of FIG. 1 and a cross-sectional perspective view of the removable cap, respectively, according to an example embodiment of the present disclosure.

FIG. 29 is a cross-sectional perspective view of the removable cap of FIGS. 28*a-b* connected to a delivery member cover, according to an example embodiment of the present disclosure.

FIG. 30 is a cross-sectional perspective view of the removable cap of FIGS. 28*a-b* connected to a main body, according to an example embodiment of the present disclosure.

FIG. 31 is a cross-sectional perspective view of the removable cap of FIGS. 28*a-b* connected to an RNS remover, according to an example embodiment of the present disclosure.

FIGS. 36*a-c* depict example cross-sectional views taken at the dose knob of the medicament delivery device of FIG. 1, according to an example embodiment of the present disclosure.

FIG. 37 depicts a perspective view of the rear shell of the medicament delivery device of FIG. 1, according to an example embodiment of the present disclosure.

FIG. 38 illustrates an example separating rib, according to an example embodiment of the present disclosure.

DETAILED DESCRIPTION

Figure 1:
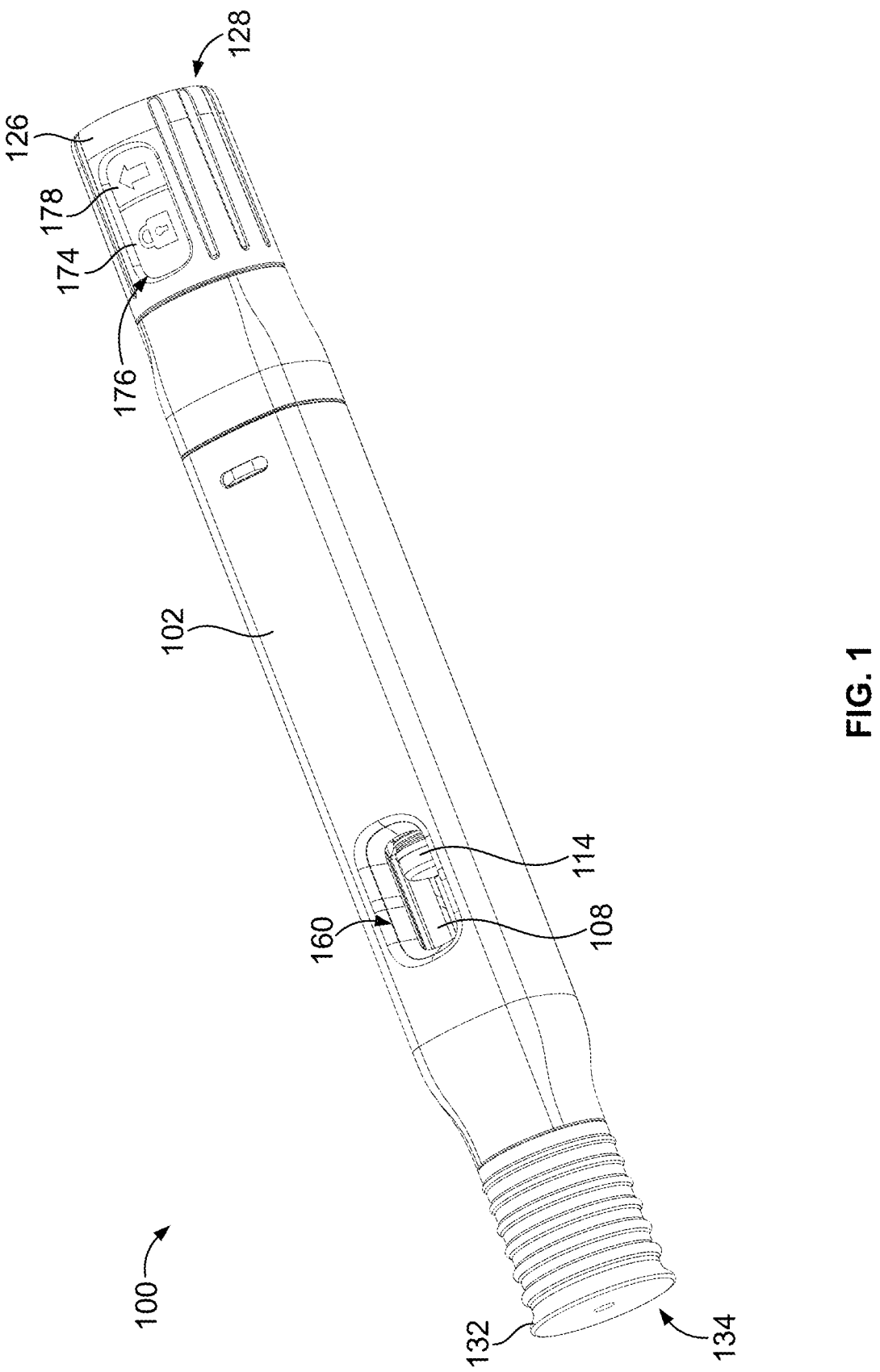
FIG. 1 illustrates an example medicament delivery device, according to an example embodiment of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The disclosed medicament delivery device provides a safe, intuitive and user-friendly device for delivering a dose of medicament. In accordance with example embodiments of the present disclosure, a medicament delivery device is configured to deliver a variable single dose of medicament subcutaneously from a preinstalled and prefilled syringe. The dose is set prior to removing the cap of the medicament delivery device. During removal of the cap, the autoinjector is automatically primed. Further, the medicament delivery is activated by the user when the delivery member cover is pressed on the medicament delivery site. After medicament delivery of the dose of medicament, the medicament delivery device automatically locks the delivery member cover to prevent e.g. needle stick injuries and the autoinjector is disposed.

FIG. 1 generally illustrates an example medicament delivery device 100 that is capable of setting and delivering a variable single dose of medicament. In particular, FIG. 1 illustrates medicament delivery device 100 in an initial state prior to medicament delivery. Further, FIG. 2a illustrates a top cross-sectional view of medicament delivery device 100 in the initial state, and FIG. 2b illustrates a side cross-sectional view of medicament delivery device 100 in the initial state.

Figures 2A, 2B:
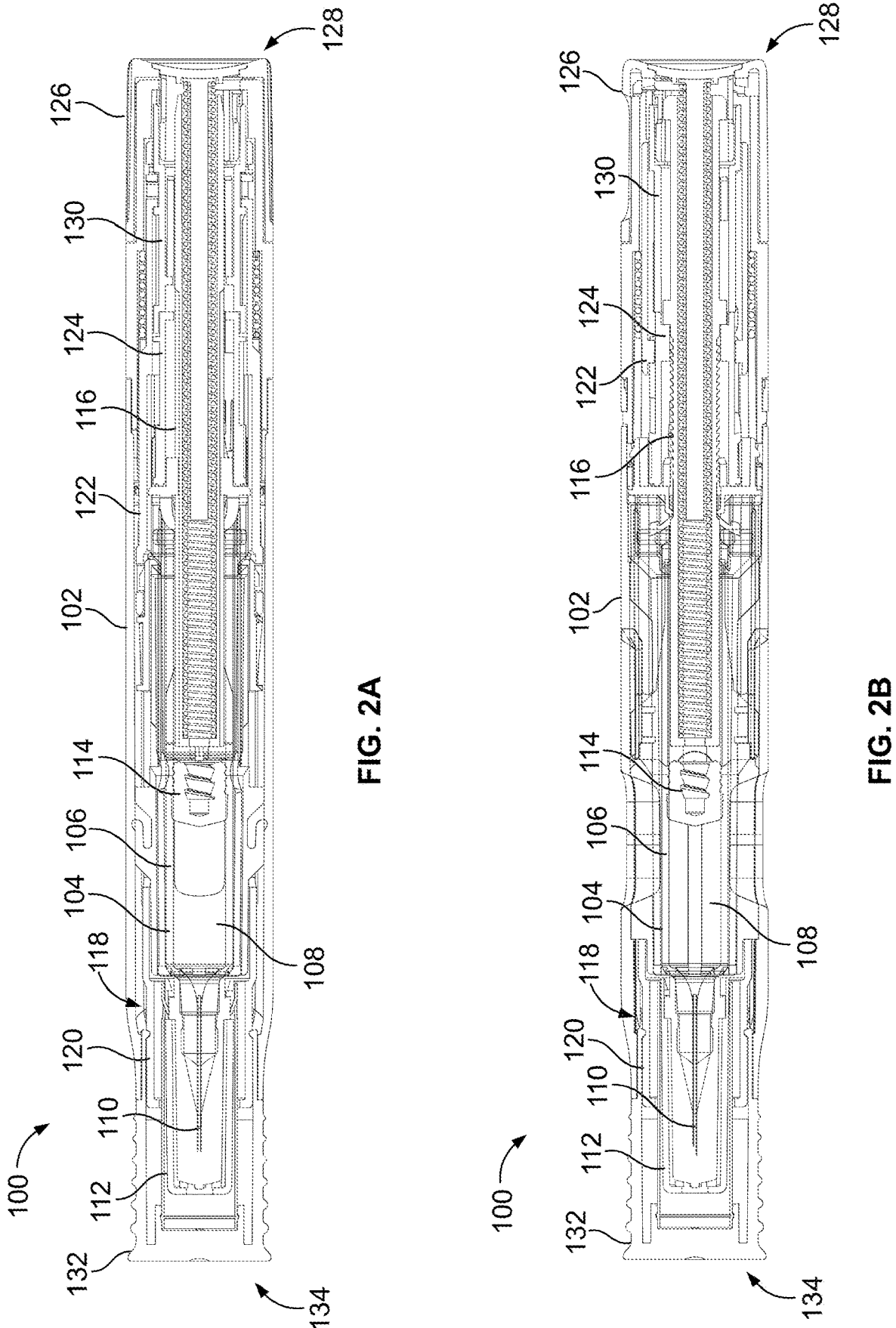
FIG. 2a illustrates a top cross-sectional view of the medicament delivery device of FIG. 1, according to an example embodiment of the present disclosure.
FIG. 2b illustrates a side cross-sectional view of the medicament delivery device of FIG. 1, according to an example embodiment of the present disclosure.

With reference to FIGS. 1 and 2a-b, medicament delivery device 100 includes a main body 102 and a syringe 104 arranged in the main body 102. The syringe 104 includes a syringe body 106 holding a medicament 108, a delivery member i.e. an injection needle 110, and a rigid needle shield (RNS) 112 covering the delivery member i.e. the injection needle 110. A piston 114 is disposed in the syringe body 106. The medicament delivery device 100 further includes a plunger rod 116 operatively arranged to eject the medicament 108 through the delivery member i.e. the injection needle 110 attached to the syringe 104.

Even though a syringe 104 is described in this example embodiment of FIG. 1, any suitable type of medicament 108 containing enclosure may be used in the disclosed medicament delivery device 100, such as a syringe, an ampoule, a cartridge, a container, etc. Further, the medicament may be any suitable substance used for medical treatment. In an example embodiment, the medicament is Sumatriptan, which may be used for migraine treatment.

Even though an automatic injection device is described in this example embodiment of FIG. 1, any suitable type of medicament delivery device 100 having a suitable delivery member 110 may be used in the disclosed medicament delivery device 100.

A delivery member shield unit 118 is slidably arranged in the main body 102. In this example, the delivery member shield unit 118 includes a delivery member cover 120 and a delivery member shield link 122. A tubular member 124 (hereinafter referred to as a "rotator") is arranged inside the delivery member shield unit 118. The rotator 124 is coupled to the plunger rod 116. Further, a dose knob 126 is disposed at a proximal end 128 of the medicament delivery device 100 and is configured to rotate with respect to the main body 102 for setting a dose of the medicament 108. Still further, a dose stop 130 is configured to rotate with the dose knob 126. In addition to being coupled to the dose knob 126, the dose stop 130 is coupled to the delivery member shield unit 118. For instance, the dose stop 130 includes an engagement feature configured to engage with a corresponding engagement feature on the delivery member shield unit 118.

A removable cap 132 is disposed on a distal end 134 of the medicament delivery device 100. The removable cap 132 is releasably coupled to the delivery member shield unit 118 and is configured to be locked prior to a dose of the medicament 108 being set and to be unlocked when a dose of the medicament 108 is set. For instance, prior to a dose of the medicament 108 being set, the delivery member shield unit 118 and the removable cap 132 are axially locked with respect to the main body 102. Further, after a dose of the medicament 108 is set, the delivery member shield unit 118 and the removable cap 132 are unlocked and are axially moveable with respect to the main body 102.

Figure 3:
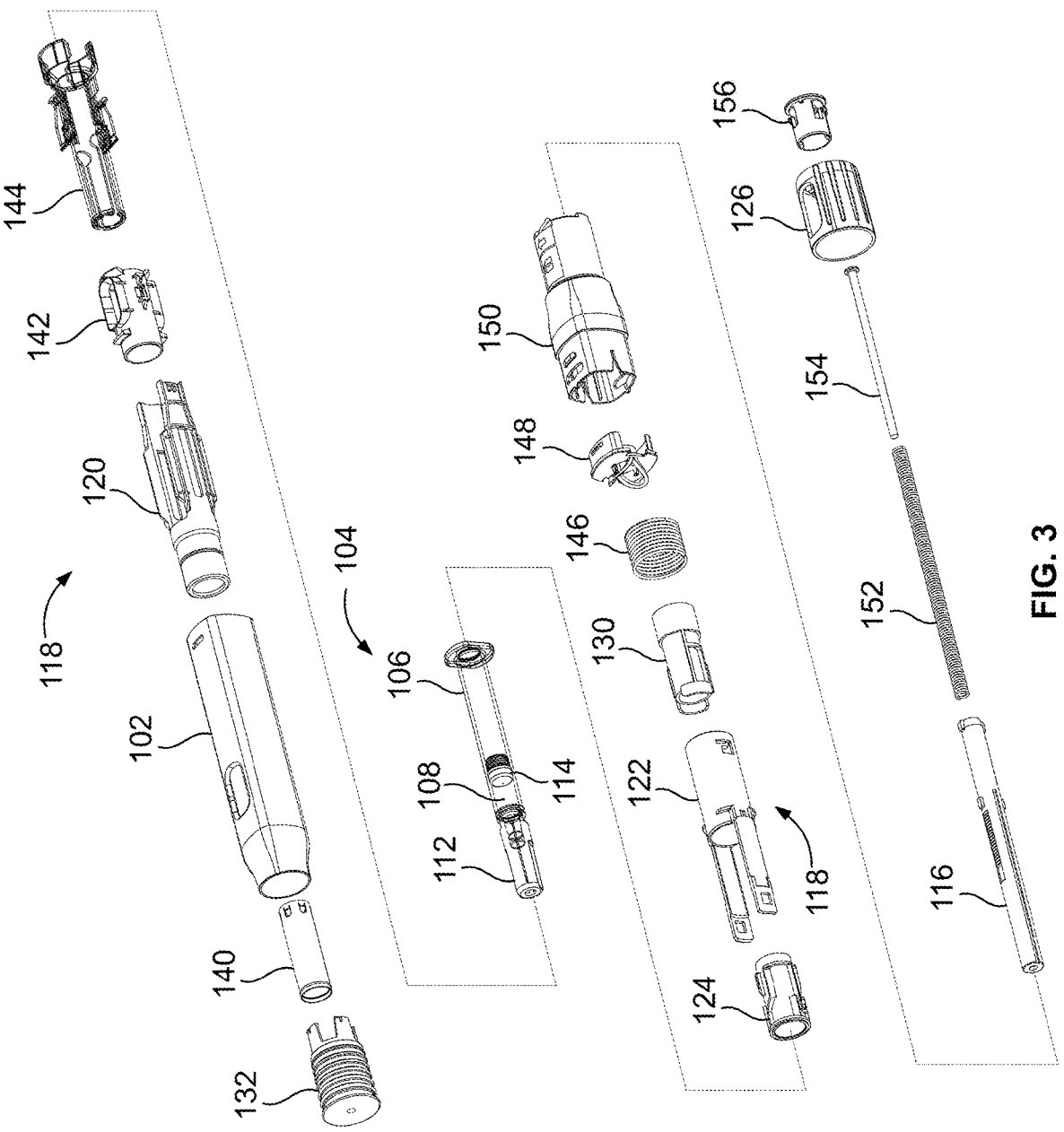
FIG. 3 illustrates an exploded view of the medicament delivery device of FIG. 1, according to an example embodiment of the present disclosure.

FIG. 3 illustrates an exploded view of medicament delivery device 100. This exploded view shows example components of medicament delivery device 100. The component parts of medicament delivery device 100 include the following components: cap 132, rigid needle shield (RNS) remover 140, main body (e.g., front shell) 102, delivery member cover 120, front shell frame 142, syringe housing 144, syringe 104, rotator 124, delivery member shield link 122, dose stop 130, delivery member cover spring 146, rear shell clip 148, rear shell 150, plunger rod 116, plunger rod spring 152, spring guide rod 154, dose knob 126, and back lid 156. It should be understood that the illustrated components are intended as an example only. In other example embodiments, fewer components, additional components, and/or alternative components are possible as well.

In order to administer a dose of medicament 108 from medicament delivery device 100, a user (i) sets a dose, (ii) removes the cap, (iii) places the device on the medicament delivery site 211, and (iv) presses the device against the medicament delivery site 211. In an example embodiment, during removal of the removable cap 132 from the medicament delivery device 100, the medicament delivery device 100 is primed. After medicament delivery is complete, the user then removes the device from the medicament delivery site 211. The delivery member cover 120 may axially extend and lock in the extended position so as to limit or prevent e.g. needle stick injury.

As shown in FIG. 1, medicament delivery device 100 includes a window 160 in the main body 102. In an example embodiment, prior to medicament delivery of the variable single dose of medicament 108, the medicament 108 and at least part of the stopper 114 is visible through the window 160. Prior to medicament delivery, a user may inspect the medicament 108 through the window 160. The ability to inspect the medicament 108 through window 160 may help to increase the safety of the medicament delivery device 100. For example, this ability may help the user confirm that the medicament delivery device 100 contains a dose of the medicament 108. This ability may also help the user confirm that the medicament delivery device 100 contains the correct type of medicament 108 that the user intends to deliver.

In this initial state prior to a dose of the medicament 108 being set, the delivery member shield unit 118 and the removable cap 132 are axially locked with respect to the main body 102. By being axially locked with respect to the main body 102, a user would be unable to remove the cap 132 and thus would be unable to administer a dose. However, by setting a dose of the medicament 108, the cap 132 is unlocked and the user is then able to remove the cap 132 from the device 100 in order to administer the dose.

The removable cap 132 and its interaction with other various components of the medicament delivery device 100 is described in greater detail with reference to FIGS. 4-7.

Figures 4, 5, 6:
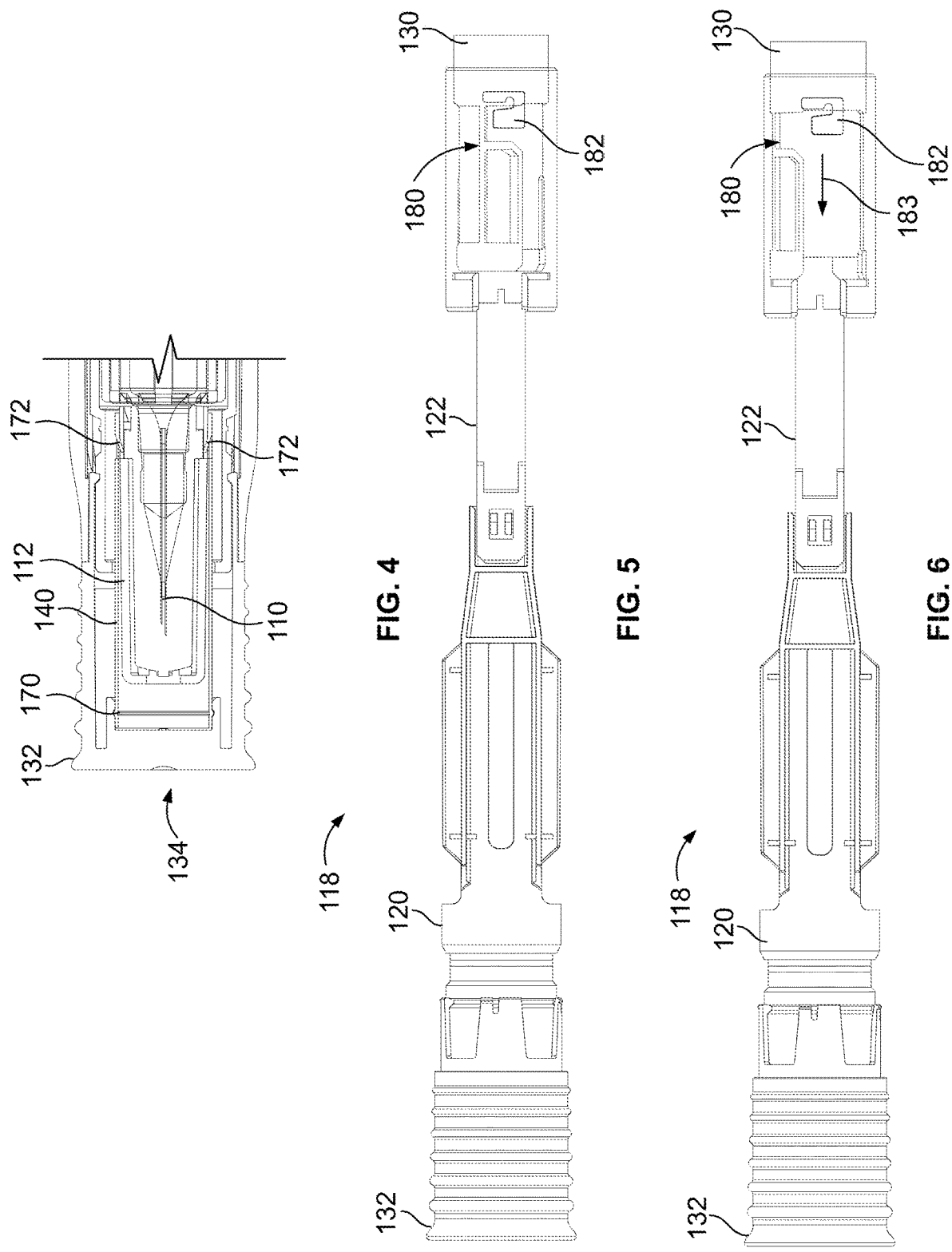
FIG. 4 illustrates a cross-sectional view of the distal end of the medicament delivery device of FIG. 1, according to an example embodiment of the present disclosure.
FIG. 5 illustrates example components of the medicament delivery device of FIG. 1, according to an example embodiment of the present disclosure.
FIG. 6 illustrates example components of the medicament delivery device of FIG. 1 during a dose setting operation, according to an example embodiment of the present disclosure.

During removal of the cap 132, the cap 132 acts to remove the RNS 112 covering the delivery member i.e. an injection needle of the syringe 104. FIG. 4 illustrates a close-up view of the distal end 134 of the medicament delivery device 100. As seen in FIG. 4, in the initial state, RNS remover 140 is fastened to the removable cap 132. The RNS remover 140 includes a first engagement feature 170 for coupling to the removable cap 132 and a second engagement feature 172 for coupling to the RNS 112. In an example embodiment, the first engagement feature 170 is a snap-fit feature and the second engagement feature 172 is a prong. The removable cap 132 is free to rotate without rotating the RNS remover 140. Therefore, prior to setting a dose, a user may rotate the removable cap 132 but the user will be unable to remove the cap 132 from the device 100. However, in another example embodiment, the removable cap 132 is locked rotationally in addition to being locked axially.

FIG. 5 illustrates example components that are configured to lock the medicament delivery device 100 when a dose is not set. Removable cap 132 is connected to delivery member shield unit 118, and delivery member shield unit 118 is connected to dose stop 130. As shown in FIG. 5, delivery member shield unit 118 includes delivery member cover 120 which is connected to delivery member shield link 122, and removable cap 132 is connected to delivery member cover 120 while delivery member shield link 122 is connected to dose stop 130. Dose stop 130 includes an engagement feature such as outwardly protruding element 180 configured to engage with a corresponding engagement feature on the delivery member shield link 122 such as an inwardly protruding element 182. Prior to a dose being set, outwardly protruding element 180 and inwardly protruding element 182 engage one another and prevent axial movement of the delivery member shield unit 118 with respect to the dose stop 130. This engagement locks the removable cap 132 such that the removable cap 132 cannot be removed from the medicament delivery device 100.

As mentioned above, dose stop 130 is configured to rotate with the dose knob 126. For instance, when a user rotates dose knob 126 to set a dose, dose stop 130 also rotates a corresponding amount. Setting the dose via dose knob 126 causes the outwardly protruding element 180 to be moved out of engagement with the inwardly protruding element 182, so as to release the engagement between the dose stop 130 and the delivery member shield unit 118. This release of the engagement between the dose stop 130 and the delivery member shield unit 118 is depicted in FIG. 6. In particular, FIG. 6 illustrates outwardly protruding element 180 moved out of engagement with the inwardly protruding element 182. After these elements have been moved out of engagement with each other, the device 100 is unlocked and the removable cap 132 and delivery member shield unit 118 are movable in the distal direction indicated by arrow 183. In order to move the cap 132 and the delivery member shield unit 118, a user may pull on the cap 132 in distal direction 183.

Figures 7, 8:
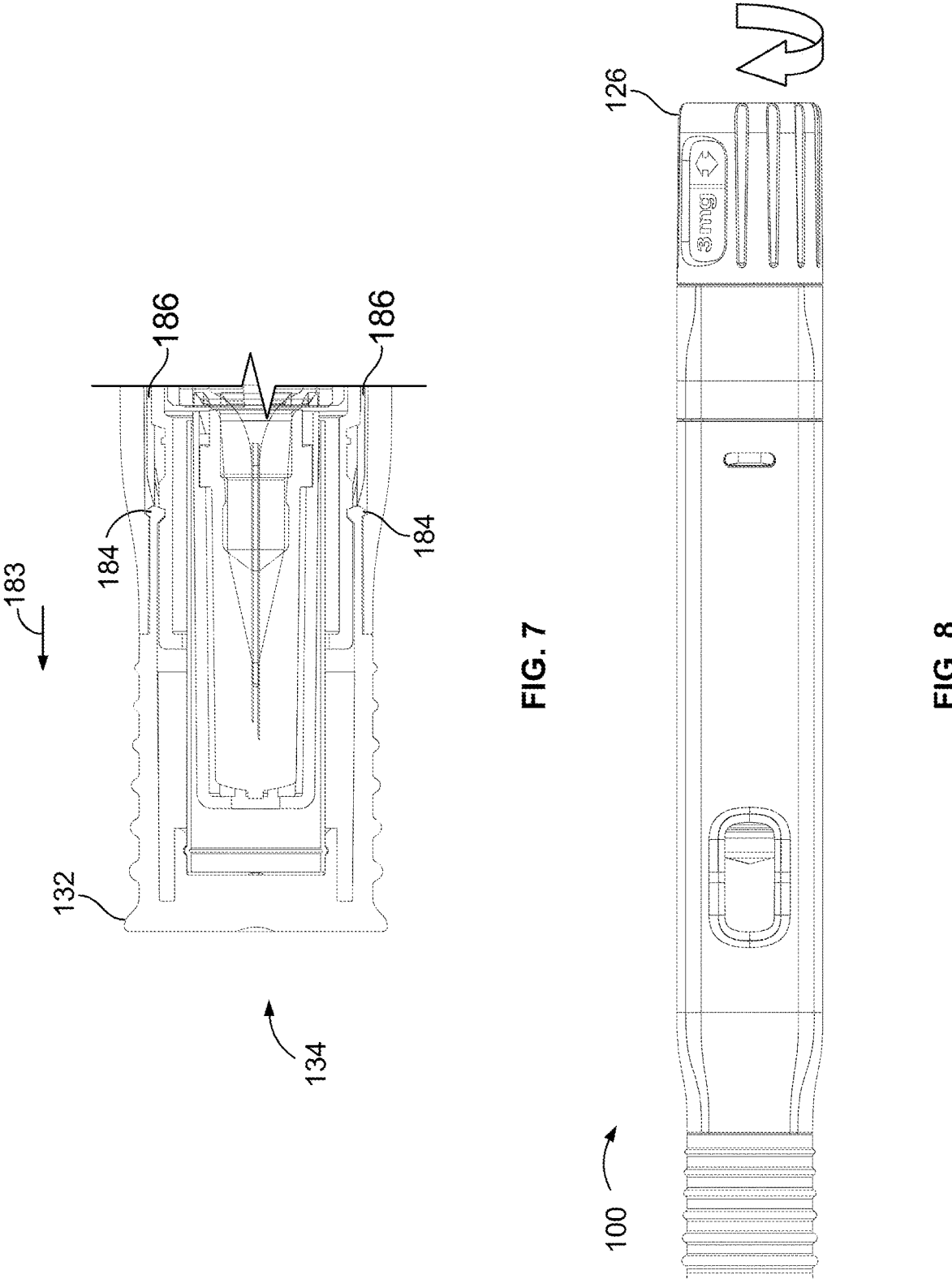
FIG. 7 illustrates a cross-sectional view of the distal end of the medicament delivery device of FIG. 1, according to an example embodiment of the present disclosure.
FIG. 8 illustrates the medicament delivery device of FIG. 1 during a dose setting operation, according to an example embodiment of the present disclosure.

The removable cap 132 may also include engagement features that interact with the main body 102 to facilitate further engagement of the removable cap 132 to the device. FIG. 7 illustrates another close up of the distal end 134 of the medicament delivery device 100. Tabs 184 on the removable cap 132 lock against the inside surface 186 of the main body 102 when the device is locked. However, when the removable cap 132 and the delivery member shield unit 118 are unlocked, this engagement between cap 132 and the main body 102 may be overcome by a user pulling the cap 132 in the distal direction 183.

In an example embodiment, the medicament delivery device 100 includes a visual indication 174 that serves to indicate that the delivery member shield unit 118 and the removable cap 132 are axially locked. For instance, as shown in FIG. 1, visual indication 174 is visible through a window 176 in the dose knob 126. While this visual indication 174 is an illustration of a lock, any suitable visual indication to illustrate that the device is locked is possible. The medicament delivery device 100 also includes visual indication 178 that indicates a movement that is capable of unlocking the medicament delivery device 100.

Figures 9, 10:
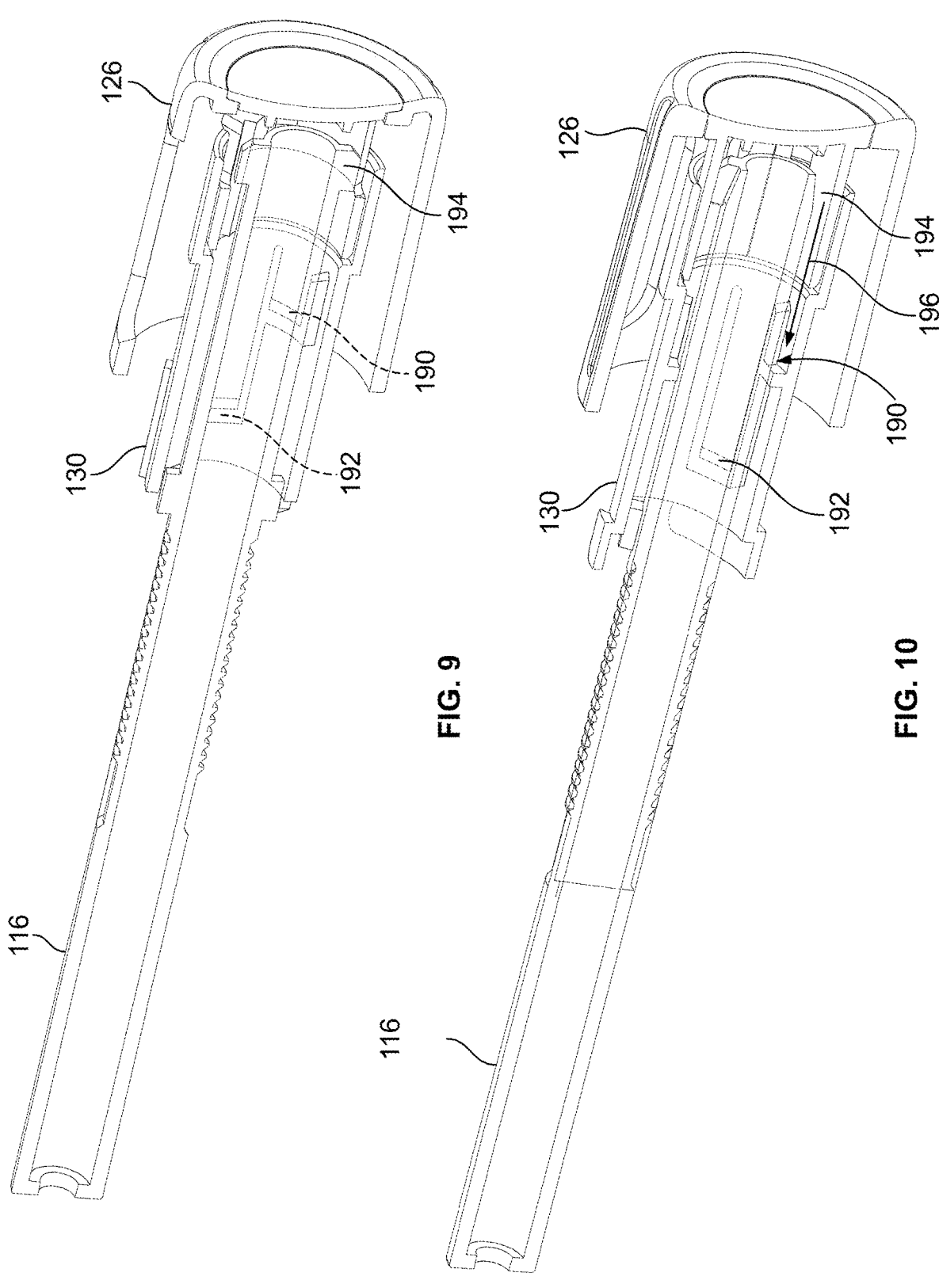
FIG. 9 illustrates example components of the medicament delivery device of FIG. 1 during a dose setting operation, according to an example embodiment of the present disclosure.
FIG. 10 illustrates example components of the medicament delivery device of FIG. 1 during a dose setting operation, according to an example embodiment of the present disclosure.

The process of setting the dose is described further with reference to FIGS. 8-10. With reference to FIG. 8, a user selects a dose by turning the dose knob 126 a given amount (e.g., 45 degrees) for a first dose value (e.g., a 3 mg dose) or a second given amount (e.g., 90 degrees) for a second dose value (e.g., a 6 mg dose). The user may dial back and forth between the various selectable doses and the locked position. As a user sets a dose and unlocks the medicament delivery device 100, the dose knob window 176 moves and covers up the visual indication 174 to reveal a dose value (as can be seen by comparing FIG. 1 and FIG. 8). Thus, the user would be aware that the device is unlocked and that a dose has been set.

In an example, the user turns the dose knob 126 clockwise to change from the locked position to a set dose position. However, in another example, the user turns the dose knob 126 counterclockwise to change from the locked position to a set dose position. Further, although the dose knob 126 is shown as being rotatable in order to set a dose, in other example embodiments the medicament delivery device is configured such that other motions (e.g., axial movement) may be used to set a dose.

As mentioned above, setting a dose unlocks the medicament delivery device 100 so that the removable cap 132 and the delivery member shield unit 118 are axially moveable. In an example, the engagement between the delivery member shield unit 118 and the dose stop 130 is fully released once the first selectable dose is reached. For instance, in an example where the user is able to select between a first selectable dose and a second selectable dose (e.g., a 3 mg dose and a 6 mg dose), the engagement between the delivery member shield unit 118 and the dose stop 130 is released when the first selectable dose (e.g., the 3 mg dose) is selected.

In addition to unlocking the cap 132 by causing the outwardly protruding element 180 to be moved out of engagement with the inwardly protruding element 182 (as shown in FIG. 6), dialing the dose via dose knob 126 also positions the dose stop 130 in the correct position for the device 100 to administer the set dose. In an example embodiment, the dose stop 130 has pockets in its inside surface that serve to, during medicament delivery, stop the plunger rod 116 travel for the selected dose. Example pockets are shown in FIG. 9, which depicts a perspective cross-sectional view of plunger rod 116, dose stop 130, and dose knob 126. As shown in FIG. 9, dose stop 130 includes a pocket formed by stop rib 190 and a pocket formed by stop rib 192. Each stop rib corresponds to a different size of dose. For instance, stop rib 190 corresponds to the first dose value (e.g., a 3 mg dose) and stop rib 192 corresponds to the second dose value (e.g., a 6 mg dose).

Plunger rod 116 is radially locked with respect to the main body 102 and includes a protrusion 194 that is configured to interact with the stop ribs 190, 192 of the dose stop 130. FIG. 9 depicts the medicament delivery device 100 before the dose knob 126 is turned to the first dose value. In particular, the protrusion 194 is just about to line up with the pocket comprising stop rib 190. FIG. 10 depicts the medicament delivery device 100 when the dose knob 126 is fully turned to the first dose value. In this position where the dose knob 126 is at the first dose value, the plunger rod 116 will be able to move distally during medicament delivery as indicated by arrow 196 until the protrusion 194 reaches stop rib 190. Further, if dose knob 126 were rotated to the second dose value, protrusion 194 would line up with stop rib 192 rather than stop rib 190. This would allow the device to deliver the larger second dose value. The dose medicament delivery process will be described in greater detail below.

Prior to delivering the dose, the removable cap 132 is removed from the medicament delivery device 100. As mentioned above, after setting the dose, the removable cap 132 is unlocked and can be removed. In order to remove the cap 132 from the medicament delivery device 100, a user may pull the removable cap 132 in a distal direction 183. This pulling action will cause both the cap 132 and delivery member shield unit 118 to move in the distal direction 183. At a given point, the delivery member shield unit 118 will reach a travel limit. In an example, the delivery member shield unit 118 includes an axial stop that limits the distal travel of the delivery member shield unit 118. The user may continue to pull the cap 132 in the distal direction 183 and this movement will cause the removable cap 132 to disengage from the delivery member shield unit 118.

Removing the cap 132 will also remove the RNS 112 from the syringe 104. In particular, as shown in FIG. 4, prongs on the RNS remover 140 interact with corresponding engagement features on the RNS 112. When the cap 132 is moved in the distal direction 183, the prongs and the corresponding engagement features remain engaged and thus the RNS 112 is removed when the cap 132 is removed. By removing the RNS 112 from the syringe 104, a delivery member, i.e. an injection needle 110 will be accessible for piercing the medicament delivery site 211 after the medicament delivery process is initiated.

Further, in an example embodiment, this action of removing the cap 132 will cause the medicament delivery device 100 to be automatically primed. By automatically priming the device during this removal action, the user will not need to undertake a separate action to prime the device, thereby improving both ease of operation of the device and safety of the device. In an example embodiment, pins 202 on the inside of the delivery member shield link 122 travel in a track 200 on the rotator 124 that cams and turns the rotator 124. The rotation of the rotator 124 releases the plunger rod 116 which is resting on shelves on the inside of the rotator 124. The plunger rod 116 travels a preset distance to a next set of shelves. After this automatic priming, the device is ready for medicament delivery. In an example, priming of the device involves ensuring that the plunger rod 116 is in contact with stopper 114 so that the correct amount of the medicament 108 can expelled from the device. In an example, in order to ensure that the plunger rod 116 is in contact with stopper 114, the medicament delivery device 100 is configured to expel expelling a priming portion of the medicament 108 from the medicament delivery device 100. An example priming portion is between 0.05 ml and 0.2 ml. However, other suitable priming portions are possible as well.

Figures 11, 12:
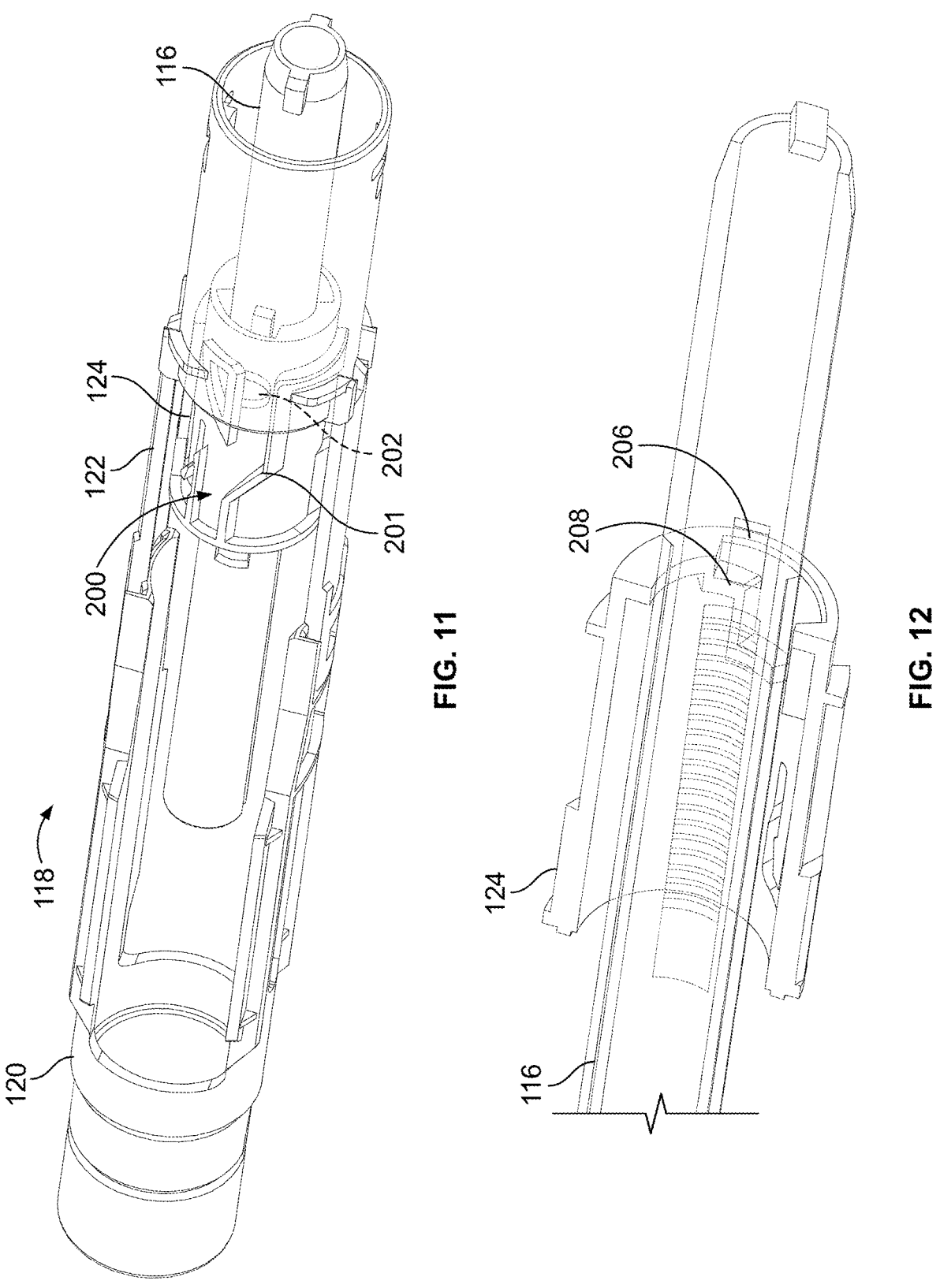
FIG. 11 illustrates example components of the medicament delivery device of FIG. 1 during removal of the cap, according to an example embodiment of the present disclosure.
FIG. 12 illustrates example components of the medicament delivery device of FIG. 1 during removal of the cap, according to an example embodiment of the present disclosure.
Figures 13, 14:
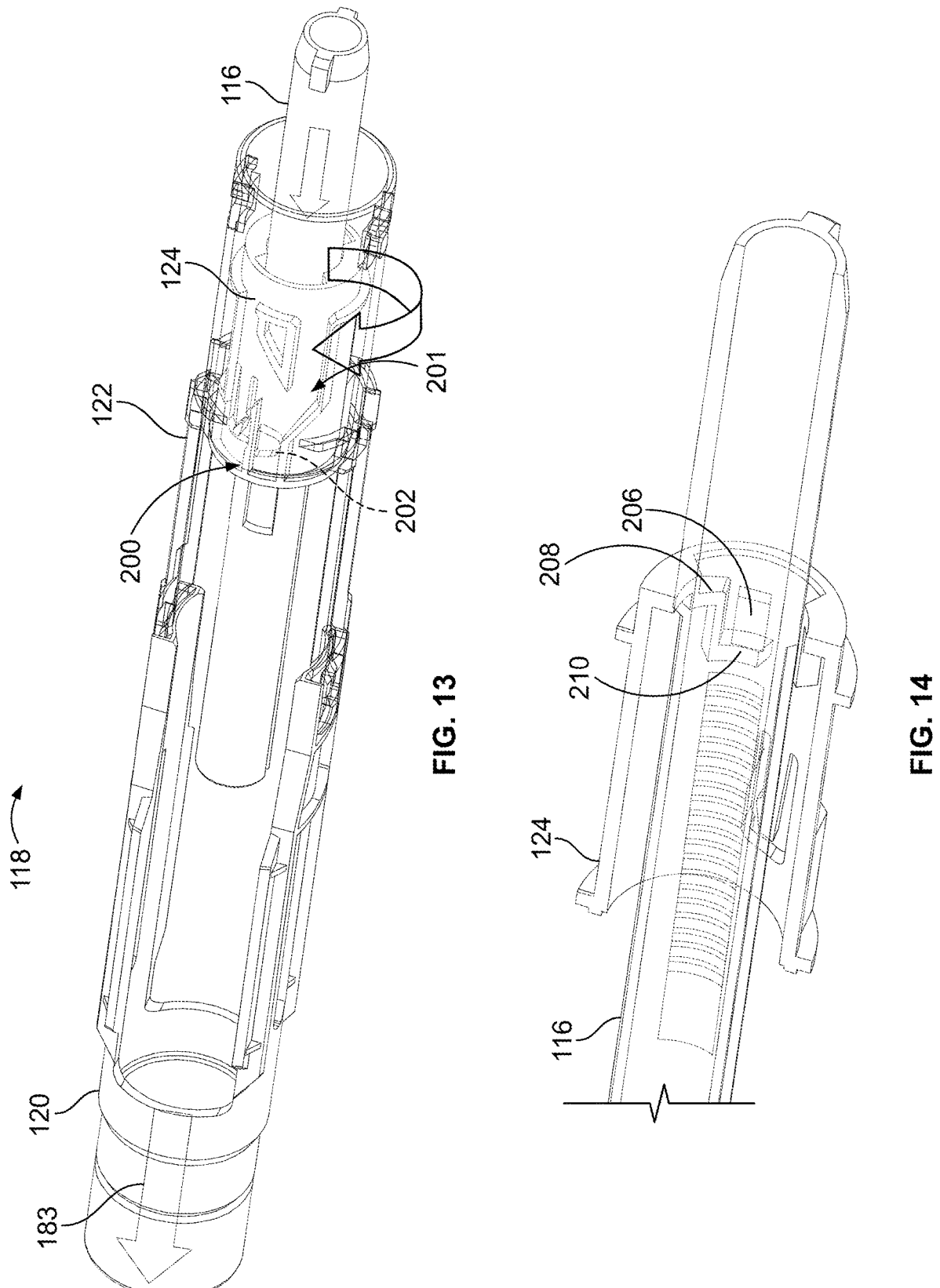
FIG. 13 illustrates example components of the medicament delivery device of FIG. 1 during removal of the cap, according to an example embodiment of the present disclosure.
FIG. 14 illustrates example components of the medicament delivery device of FIG. 1 during removal of the cap, according to an example embodiment of the present disclosure.

This automatic priming of the device is further described with reference to FIGS. 11-14. As shown in FIG. 11, rotator 124 is arranged inside the delivery member shield unit 118 and is coupled to the plunger rod 116. Rotator 124 includes a track 200. The delivery member shield unit 118 comprises a pin 202 configured to interact with the track 200 of the rotator 124. During removing of the removable cap 132, the delivery member shield unit 118 moves in the distal direction 183 and the pin 202 on the delivery member shield unit 118 travels in a first portion 201 of the track 200 on the rotator 124 so as to cause rotation of the rotator 124. The rotation releases the plunger rod 116 thereby allowing the plunger rod 116 to travel a predetermined distance so as to prime the medicament delivery device 100. In an example, the predetermined distance is a distance between rib 208 and rib 210, which are each disposed on an inner surface of the tubular member 124. In particular, rotation of the rotator 124 moves the protrusion 206 on the plunger rod 116 off of rib 208 (see FIG. 12). Plunger rod 116 is then able to move, under a force such as a spring force, distally in distal direction 183 until protrusion 206 interacts with rib 210 (see FIGS. 13 and 14). The movement of the plunger rod 116 in distal direction 183 will cause the plunger rod 116 to act on stopper 114 so as to prime the device.

In an example embodiment, after the removable cap 132 is removed and the device 100 is primed, the user is given the option to change between different selectable dose sizes but is prevented from returning the dose dial 126 to the zero dose, locked position. For instance, in the example where the user is able to select between a first selectable dose and a second selectable dose (e.g., a 3 mg dose and a 6 mg dose), the user may change between the first selectable dose and the second selectable dose (e.g., a 3 mg dose and a 6 mg dose) after removing the cap 132. However, the user may be prevented from returning the dose knob 126 to go back to the visual indication 174 (i.e., padlock symbol) (see FIG. 37) at this stage, as the dose selecting mechanism may be configured to not allow such a movement.

Figure 35A:
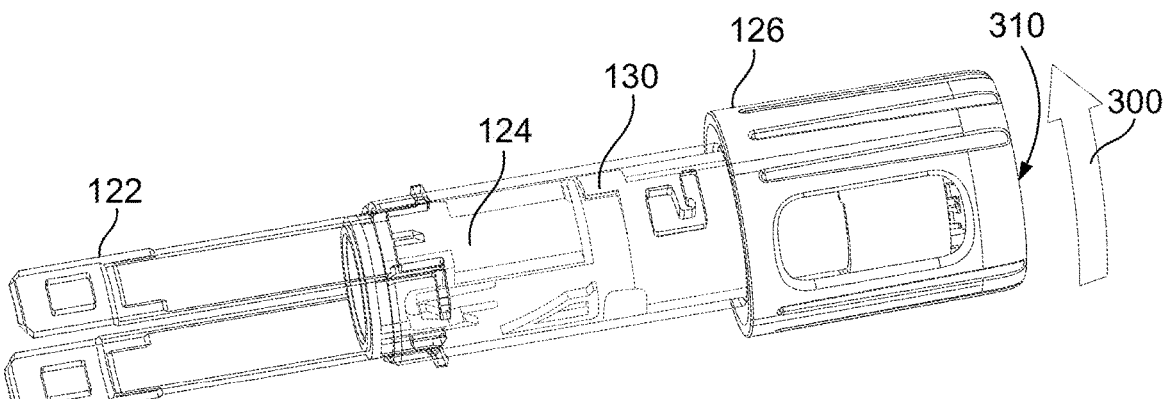
FIG. 35*a* illustrates example components of the medicament delivery device of FIG. 1 when the dose knob is positioned at a first selectable dose, according to an example embodiment of the present disclosure.

This example embodiment is described further with reference to FIGS. 35a through 37. It should be understood that other arrangements are possible as well. FIG. 35a depicts various components of the medicament delivery device 100 when the dose knob 126 is positioned at the first selectable dose after the removable cap 132 has been removed. Further, FIG. 35b depicts when the dose knob 126 is positioned at the second selectable dose after the removable cap 132 has been removed. Still further, FIGS. 36a-c depict section cut views of the dose knob 126 showing the locked, first selectable dose, and second selectable dose respective positions. Yet still further, FIG. 37 shows a perspective view of the rear shell.

Figure 35B:
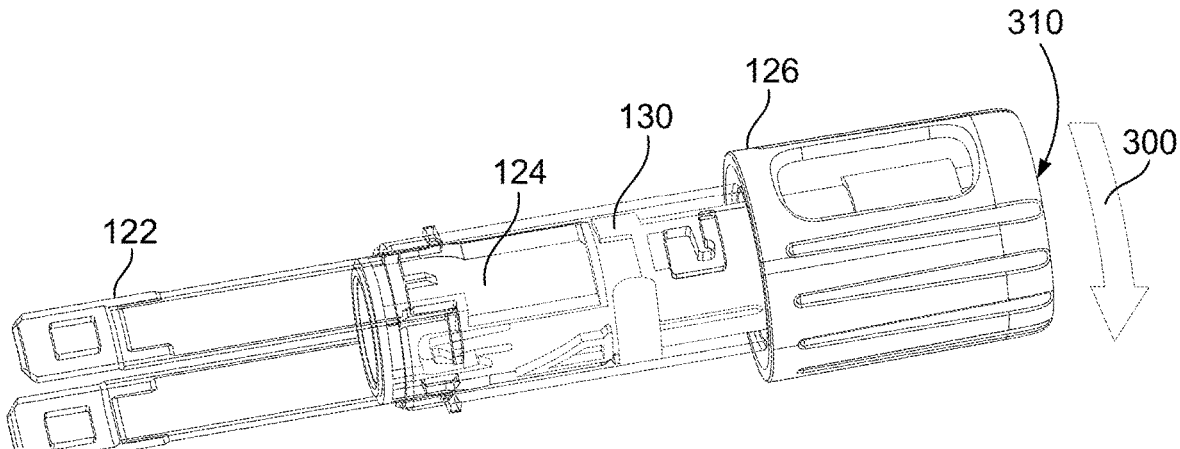
FIG. 35*b* illustrates example components of the medicament delivery device of FIG. 1 when the dose knob is positioned at a second selectable dose, according to an example embodiment of the present disclosure.

In particular, FIG. 35a depicts delivery member shield link 122, rotator 124, dose stop 130, and dose knob 126. As indicated by arrow 300, the dose knob 126 may be rotated to select the second selectable dose, but the dose knob 126 may not be rotated to the zero dose position. The user can change to the second selectable dose (e.g., the 6 mg dose) and cannot dial back to the locked state due to a rib on the dose stop 130 and the inside rib features on the radially locked delivery member shield link 122. Further, FIG. 35b depicts when the dose knob 126 is positioned at the second selectable dose. As indicated by arrow 302, the dose knob 126 may be rotated to select the first selectable dose. However, the dose knob 126 may not be rotated to set a higher dose or to the zero dose position. The user can change to the first selectable dose (e.g., the 3 mg dose) and cannot dial further as the dose knob 126 bottoms out with rib features inside the rear shell.

FIGS. 36a-c depict section cut views of the dose knob 126 showing locked, first selectable dose, and second selectable dose respective positions. In these Figures, dose knob window position 310 is shown. As shown in FIG. 36a, in the locked position, the dose knob 126 can be rotated as indicated by arrow 314. Further, as shown in FIG. 36b, after the cap is removed, the dose knob 126 can be rotated as indicated by arrow 316. Further, as shown in FIG. 36*c*, after the cap is removed, the dose knob 126 can change to the 3 mg dose and cannot dial further as the dose knob 126 bottoms out with rib features inside the rear shell. Example rib features 304 and 306 are shown in FIG. 36*c*, and an example rear shell stop feature 308 is shown in FIGS. 36*a-c* and 37.

In another example embodiment, after the removable cap 132 is removed and the device is primed, the set dose cannot be changed. In an example, a separating rib 318 can be added to lock the initially set dose so that the user cannot dial between the two doses after removing the cap 132. For instance, an example position for separating rib 318 is shown in FIG. 38. Other arrangements are possible as well.

Figure 15:
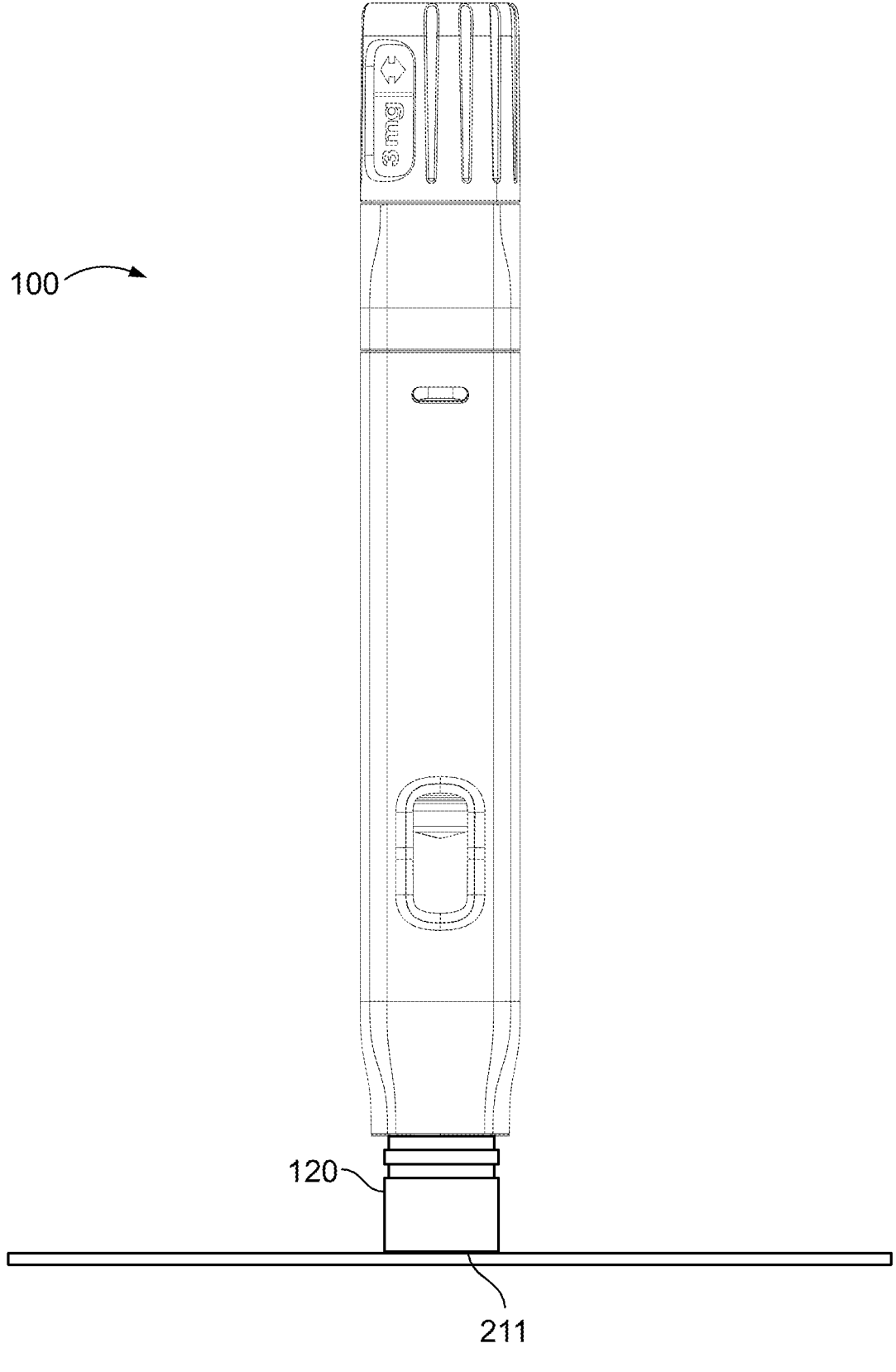
FIG. 15 illustrates the example medicament delivery device of FIG. 1 during medicament delivery, according to an example embodiment of the present disclosure.

After the removable cap 132 is removed and the device is automatically primed, the user may then initiate the medicament delivery process. To initiate the medicament delivery process, the user places the medicament delivery device 100 on an medicament delivery site 211, such as medicament delivery site 211 as shown in FIG. 15. The user manually inserts the delivery member i.e. an injection needle 110 into the medicament delivery site 211 and activates the device when the delivery member cover 120 is pressed onto the medicament delivery site 211. The device 100 is configured to automatically deliver the selected dose after being activated by the user. FIGS. 16-21 depict example components of the medicament delivery device 100 during the medicament delivery process.

Figure 16:
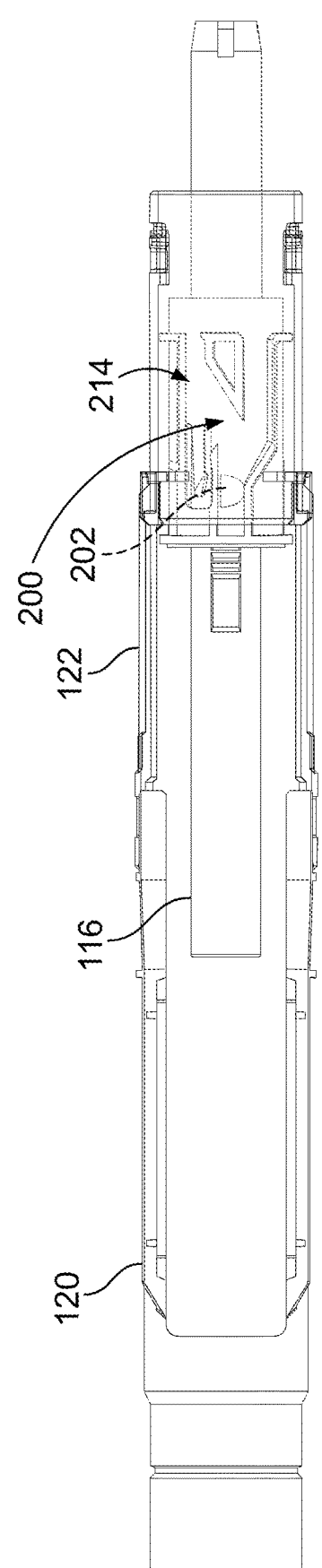
FIG. 16 illustrates example components of the medicament delivery device of FIG. 1 during medicament delivery, according to an example embodiment of the present disclosure.
Figure 17:
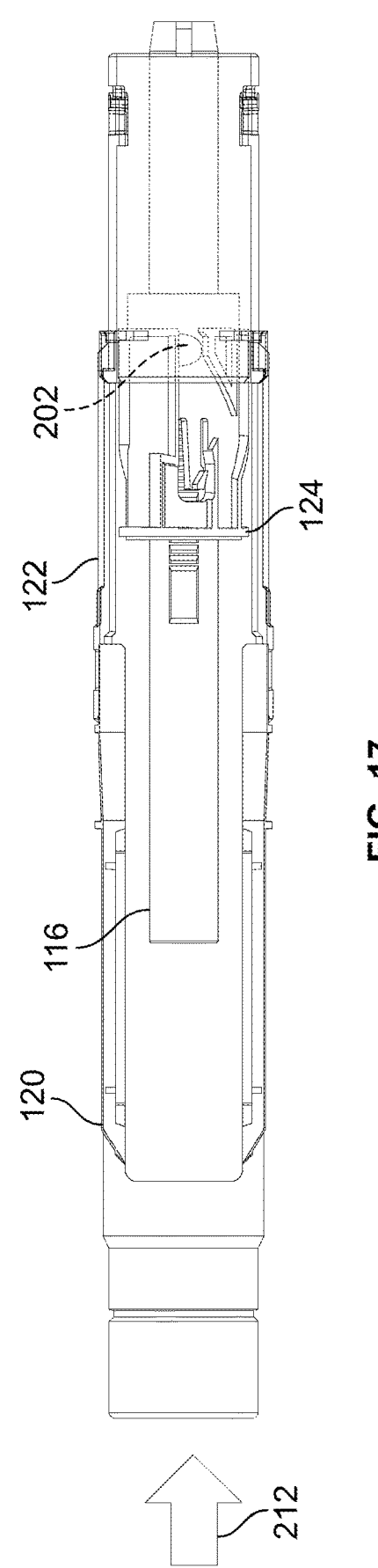
FIG. 17 illustrates example components of the medicament delivery device of FIG. 1 during medicament delivery, according to an example embodiment of the present disclosure.
Figures 18, 19:
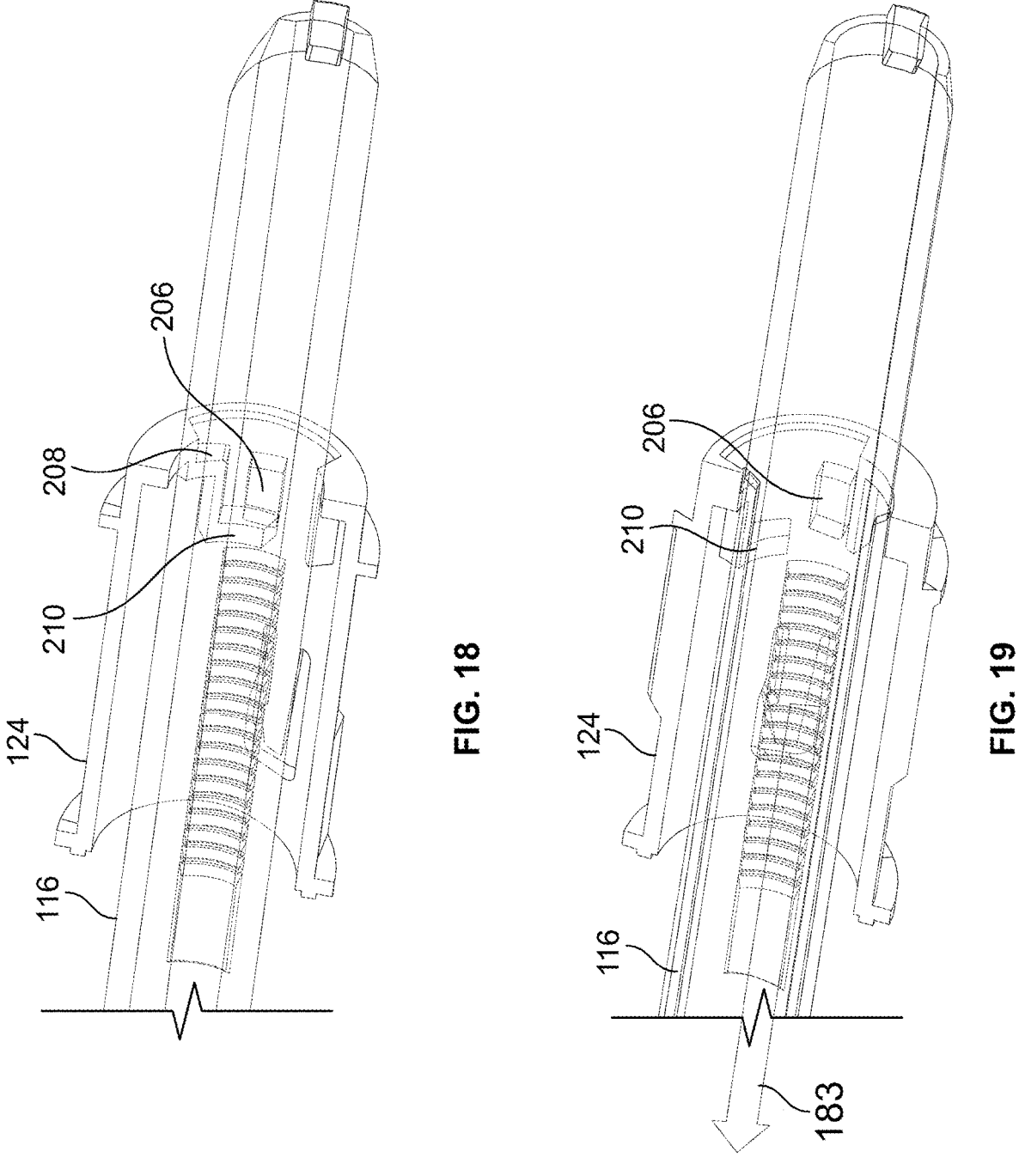
FIG. 18 illustrates example components of the medicament delivery device of FIG. 1, according to an example embodiment of the present disclosure.
FIG. 19 illustrates example components of the medicament delivery device of FIG. 1 during medicament delivery, according to an example embodiment of the present disclosure.

As seen by comparing FIGS. 16-17, the delivery member cover 120 which is connected to the delivery member shield link 122 rotates the rotator 124 as it moves axially in the proximal direction 212 (e.g., when the user pushes the device against the medicament delivery site 211). Pin 202 interacts with a second portion 214 of track 200 on the rotator 124. When the rotator 124 turns, the rotator 124 releases the plunger rod 116 which is sitting on rib 210 inside the rotator 124 (this release can be seen by comparing FIGS. 18 and 19). When plunger rod 116 is no longer interacting with rib 210, the plunger rod 116 can move in distal direction 183 (as shown in FIG. 19). This movement in the distal direction 183 will cause the dose of medicament 108 to be delivered.

Figures 20, 21:
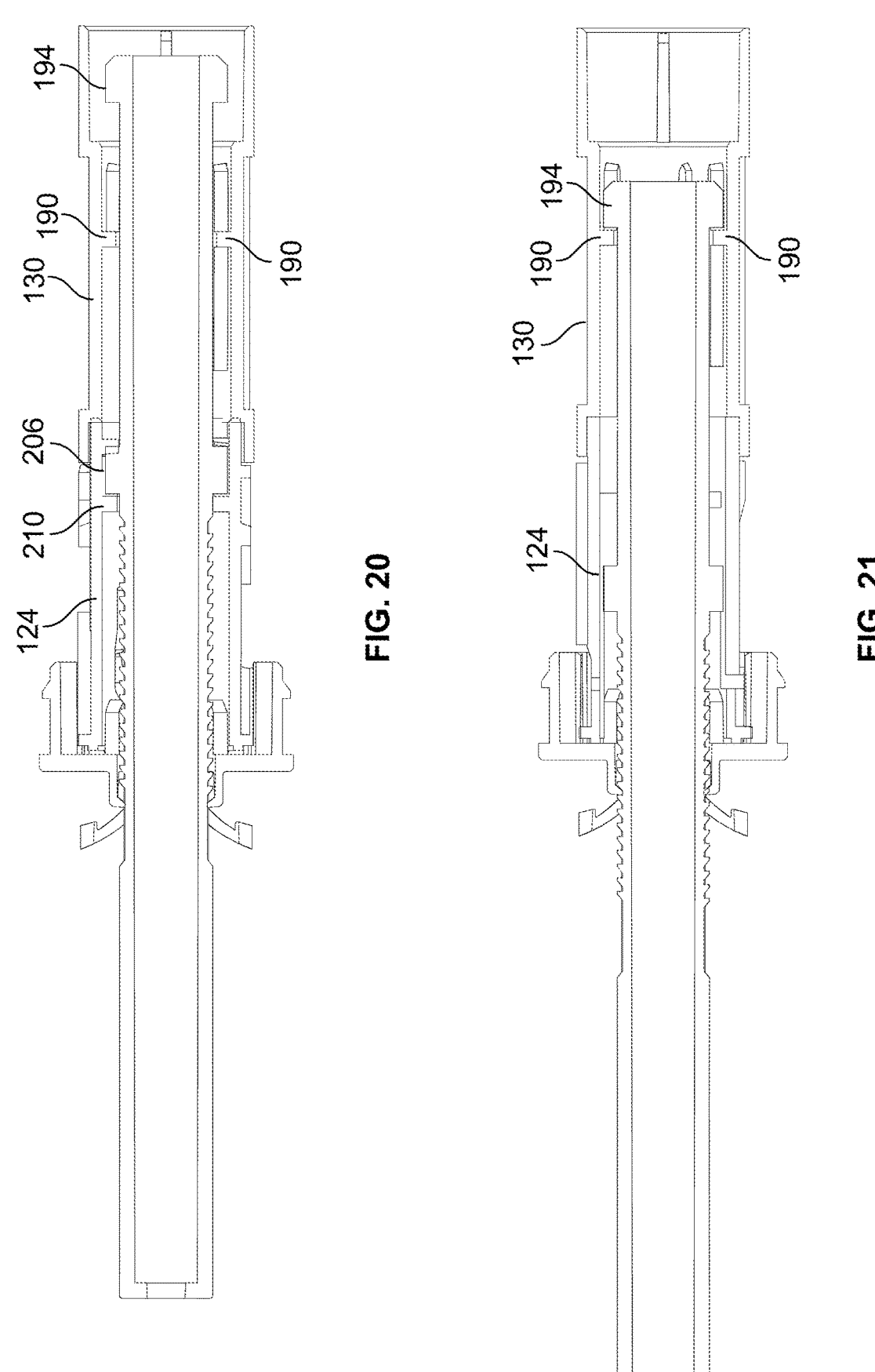
FIG. 20 illustrates example components of the medicament delivery device of FIG. 1 during medicament delivery, according to an example embodiment of the present disclosure.
FIG. 21 illustrates example components of the medicament delivery device of FIG. 1 during medicament delivery, according to an example embodiment of the present disclosure.

FIGS. 20 and 21 show movement of the plunger rod 116 during dose delivery. The plunger rod 116 will move the stopper 114 in the distal direction 183 until the set dose is fully dispensed. At the beginning of the medicament delivery process, the protrusion 206 is interacting with the priming rib 210. However, movement of the rotator 124 removes this interaction and the plunger rod 116 can move in the distal direction 183 until the protrusion 194 interacts with the stop rib(s) for the selected dose, such as stop rib 190 or 192. For instance, with reference to FIG. 21, protrusion 194 of the plunger rod 116 interacts with stop rib 190 and this stops distal travel of the plunger rod 116. At this point, the selected dose has been delivered. In an example embodiment, during dose delivery, the user can hear and/or feel an audible and/or tactile feedback (e.g., clicking) throughout the dose delivery.

After medicament delivery is complete, the device is removed from the medicament delivery site 211. In an example, the end of medicament delivery may be indicated by the audible/tactile clicking having stopped. In another example embodiment, for at least some doses (e.g., doses less than the maximum selectable dose), the stopper and plunger rod may be visible in the main body window when medicament delivery is complete. In such an example, the end of delivery may be indicated by the plunger rod and plunger having stopped moving. In another example (e.g., when the highest possible dose is delivered), the stopper is no longer visible through the main body window when medicament delivery is complete. In such an example, the device may be configured such that the end of delivery is indicated by the stopper no longer being visible through the main body window. Other indications of dose delivery being complete are possible as well.

Figures 22, 23, 24:
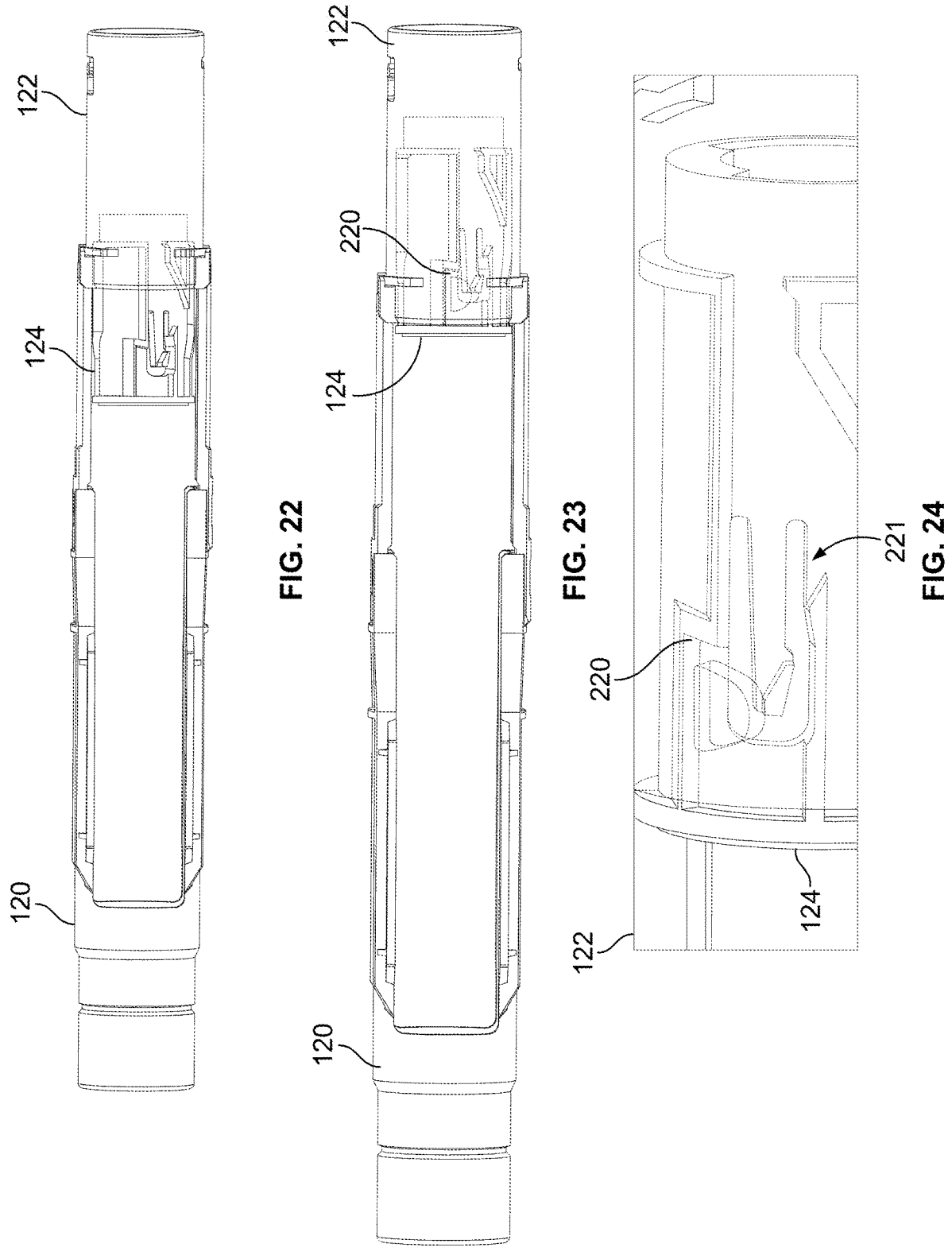
FIG. 22 illustrates example components of the medicament delivery device of FIG. 1 during removal of the device from the medicament delivery site, according to an example embodiment of the present disclosure.
FIG. 23 illustrates example components of the medicament delivery device of FIG. 1 during removal of the device from the medicament delivery site, according to an example embodiment of the present disclosure.
FIG. 24 illustrates example components of the medicament delivery device of FIG. 1 during removal of the device from the medicament delivery site, according to an example embodiment of the present disclosure.

After the user removes the medicament delivery device 100 from the medicament delivery site 211, the delivery member cover 120 will extend outward and lock into place. This extension and locking may limit or prevent e.g. needle stick injuries. When the medicament delivery device 100 is removed from the medicament delivery site 211, the delivery member cover 120 automatically extends outward in the distal direction 183 (e.g., under a force such as a spring force). As shown in FIGS. 22-24, a snap feature on the rotator 124 turns the rotator 124 enough to position the delivery member shield link pins 202 against rigid ribs on the rotator 124. Tabs 221 on the rotator 124 flex to the side when the delivery member shield link pin(s) 202 passes. Once the locking rib 220 is cleared, the rotator 124 turns slightly so that the pins 202 are positioned in front of the locking rib 220. This locks the delivery member cover 120 into place so to prevent unintended e.g. needle stick injuries. The user may then place cap 132 back on the medicament delivery device 100 and dispose of the medicament delivery device 100. Other ways of locking the delivery member cover 120 in an extended position are possible as well.

FIGS. 25-34 depict example components of the medicament delivery device 100 in further detail as well as example interactions of the components with other components.

Figures 25, 26, 27:
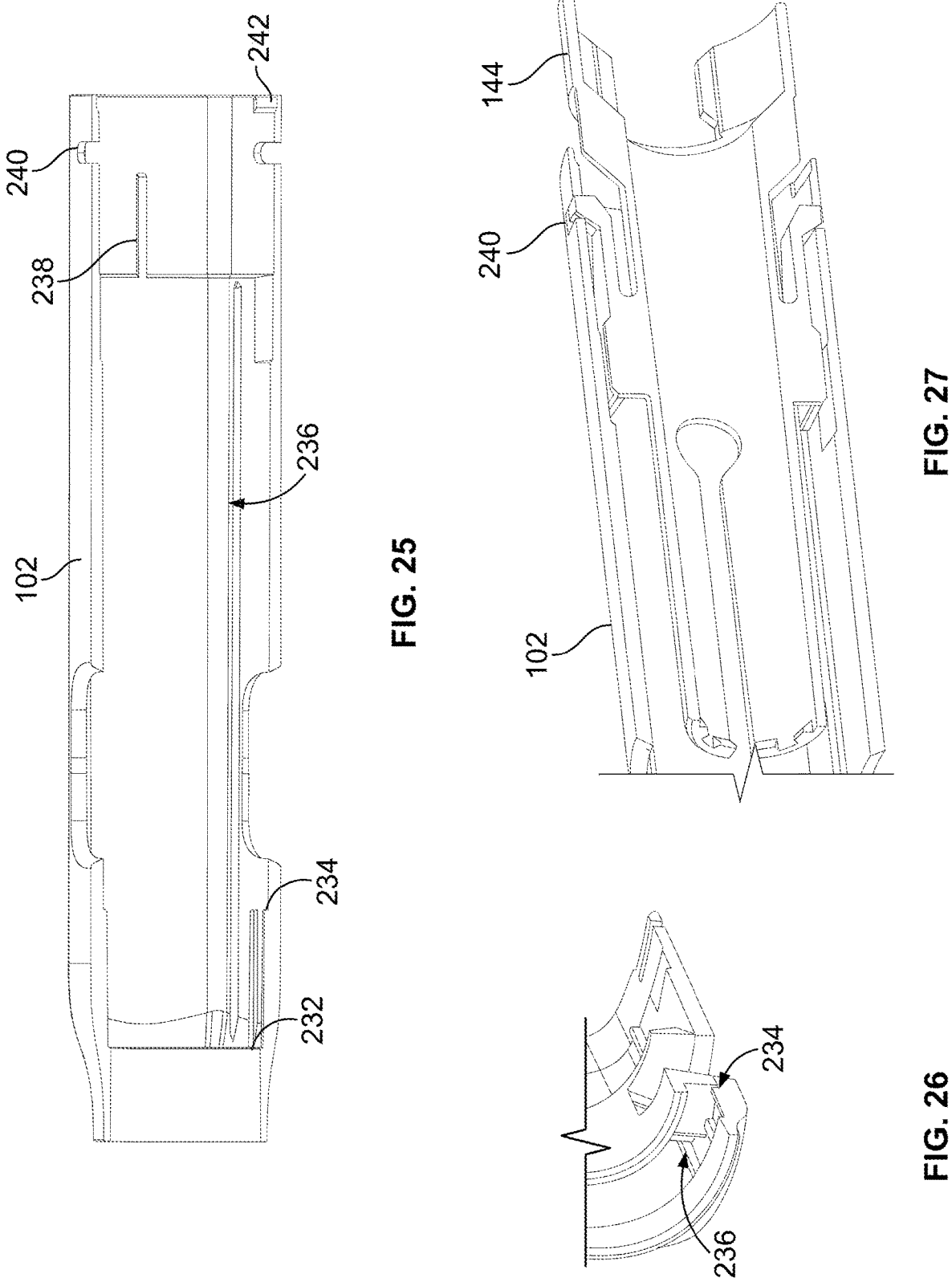
FIG. 25 is a cross-sectional perspective view of a main body of the medicament delivery device of FIG. 1, according to an example embodiment of the present disclosure.
FIG. 26 is a close-up view of axial stop ribs and radial guiding ribs of the main body of FIG. 25, according to an example embodiment of the present disclosure.
FIG. 27 is a cross-sectional perspective view of a syringe housing connected to the main body of FIG. 25, according to an example embodiment of the present disclosure.

FIG. 25 is a cross-sectional perspective view of the main body 102. Main body 102 includes an edge 230 for cap snaps, axial stop ribs 234, and radial guiding ribs 236 for the front shell frame 142 and syringe housing 144. Main body 102 further includes radial locking rib 238 for the rear shell, snap openings 240 for the syringe housing 144 and rear shell, and cutouts 242 for assembly of the rear shell. FIG. 26 is a close-up view of axial stop ribs 234 and radial guiding ribs 236 of the main body 102. FIG. 27 is a cross-sectional perspective view of the syringe housing 144 connected to the main body 102 via snap openings 240.

FIGS. 28*a-b* depict a perspective view of removable cap 132 and a cross-sectional perspective view of the removable cap 132, respectively. Removable cap 132 includes engagement feature 250 for the RNS remover 140, engagement feature 252 for the delivery member cover 120, and engagement feature 184 for the main body 102. FIG. 29 is a cross-sectional perspective view of the removable cap 132 connected to the delivery member cover 120 via engagement features 252. In particular, snap-fit engagement features 252 are connected to corresponding snap-fit engagement features 253 on the delivery member cover 120. FIG. 30 is a cross-sectional perspective view of the removable cap 132 connected to the main body 102 via engagement features 184. FIG. 31 is a cross-sectional perspective view of the removable cap 132 connected to the RNS remover 140 via engagement feature 250.

Figure 32:
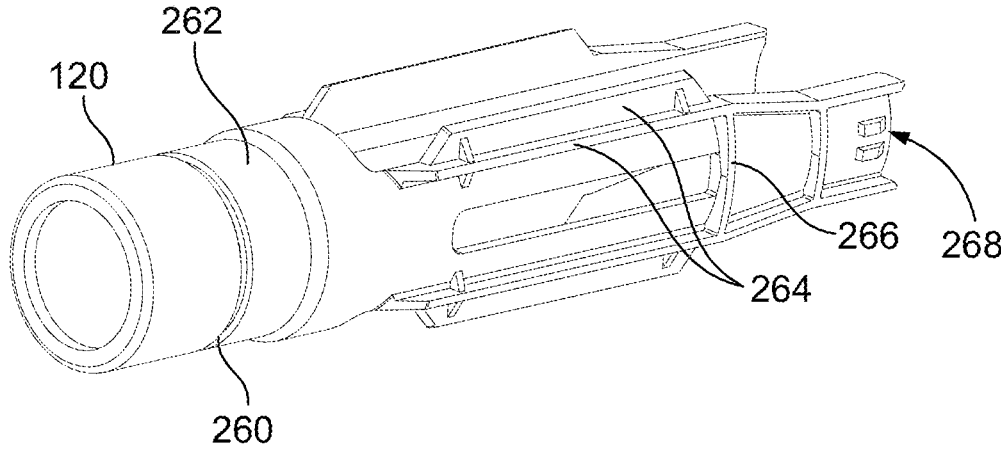
FIG. 32 is a perspective view of a delivery member cover of the medicament delivery device of FIG. 1, according to an example embodiment of the present disclosure.

FIG. 32 is a perspective view of the delivery member cover 120. Delivery member cover 120 includes engagement feature 260 for holding the cap prior to cap removal and engagement feature 262 for holding the cap after medicament delivery. Further, delivery member cover 120 includes delivery member cover guiding ribs 264, axial stop 266 for the delivery member cover 120 extension, and delivery member shield link connecting interface 268.

Figure 33:
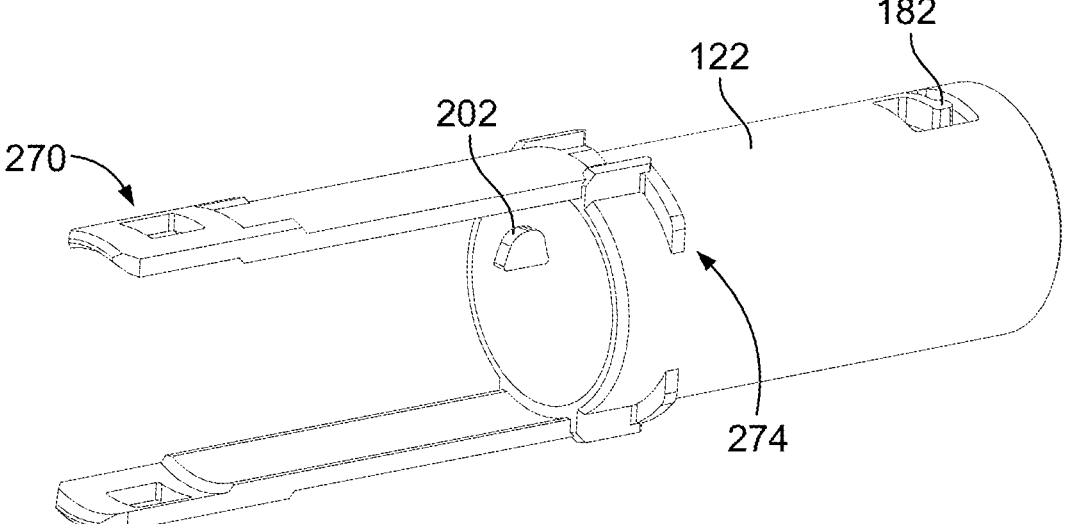
FIG. 33 is a perspective view of a delivery member shield link of the medicament delivery device of FIG. 1, according to an example embodiment of the present disclosure.

FIG. 33 is a perspective view of the delivery member shield link 122. Delivery member shield link 122 includes delivery member cover connecting interface 270 and pin 202 for traveling and camming into the rotator track 200. Delivery member shield link 122 also includes delivery member cover springs seat 274 and spring feature 182 configured to keep the dose stop 130 and delivery member shield link 122 together during sub assembly.

Figure 34:
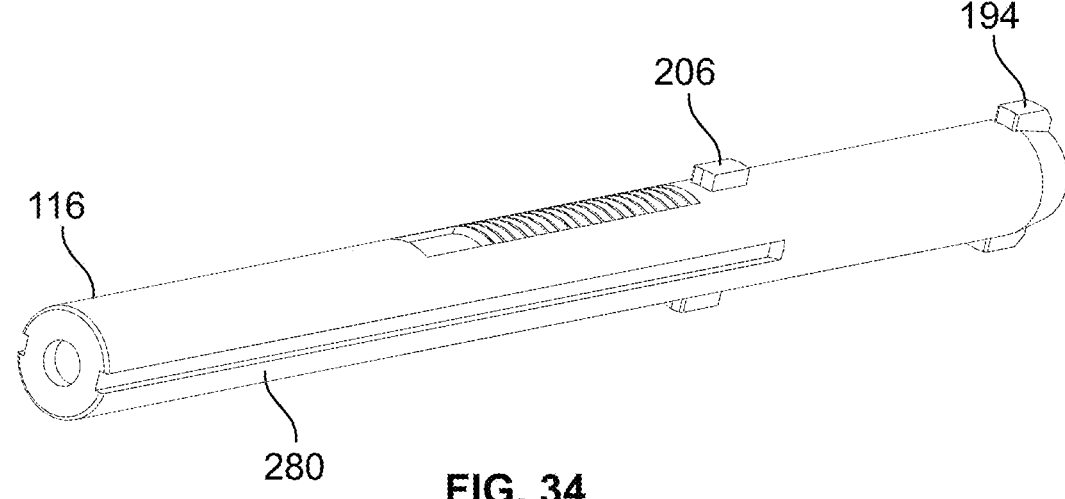
FIG. 34 is a perspective view of a plunger rod of the medicament delivery device of FIG. 1, according to an example embodiment of the present disclosure.

FIG. 34 is a perspective view of the plunger rod 116. Plunger rod 116 includes radial guidance 280, as well as protrusion 206 for priming and protrusion 194 interacting with dose stop ribs 190, 192.

As mentioned above, the medicament delivery device of the present disclosure is configured to deliver a variable single dose of medicament 108. In the example shown in the Figures, the medicament delivery device 100 is configured to allow the user to select either a first dose or a second dose. However, in other embodiments, the medicament delivery device could be configured to allow the user to select fewer doses or more doses. For instance, in an example embodiment, the user is able to select a (non-variable) single dose. In other example embodiments, the user is able to select three different doses, four different doses, five different doses, and so forth.

The embodiment described above is an automatic injector. The delivery mechanism of the automatic injector may be powered by a suitable mechanism such as a spring, compressed gas, or electrical energy. Further, in other embodiments, the medicament delivery device is a manual injector where the delivery mechanism is powered by a manual action of the user.

Further, various engagement features for are shown for providing an engagement between one or more components of the medicament delivery device. The engagement features may be any suitable connecting mechanism such as a snap lock, a snap fit, form fit, a bayonet, lure lock, threads or combination of these designs. Other designs are possible as well.

As mentioned above, removing the cap may act to automatically prime the medicament delivery device. Additionally or alternatively, removing the cap may perform other actions. For instance, in an example where the device is a dual chamber device having two different medicaments that are separated prior to medicament delivery, removing the cap may act to mix the medicaments. For example, removing the cap may cause the plunger to move a stopper inside the cartridge to a position where two substances contained in the cartridge, and initially held separated from each other by the stopper, are mixed. Other example actions upon removing the cap are possible as well.

It is to be understood that the above described and shown embodiment of the present disclosure is to be regarded as a non-limiting example and that it can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A medicament delivery device comprising:
a main body;
a syringe arranged in the main body, wherein the syringe comprises a medicament;
a delivery member shield unit slidably arranged in the main body;
a removable cap abutting the delivery member shield unit, wherein the removable cap comprises a snap-fit feature configured to releasably connect to a corresponding snap-fit feature on the delivery member shield unit; and
a plunger rod operatively arranged to eject the medicament through a delivery member attached to the syringe,
wherein, during removal of the removable cap, as a user removes the removable cap both the removable cap and delivery member shield unit move in a distal direction,
wherein the delivery member shield unit includes an axial stop that limits a distal travel of the delivery member shield unit, and
wherein as the user removes the removable cap, after the delivery member shield unit reaches the axial stop the removable cap disengages from the delivery member shield unit.

2. The medicament delivery device of claim 1, wherein the removable cap and the delivery member shield unit move together via the snap-fit feature of the removeable cap being connected to the corresponding snap-fit feature of the delivery member shield unit until the delivery member shield unit reaches the axial stop.

3. The medicament delivery device of claim 2, wherein the snap-fit feature of the removable cap comprises a first projection, and wherein the corresponding snap-fit feature on the delivery member shield unit comprises a second projection.

4. The medicament delivery device of claim 1, wherein the medicament delivery device further comprises a rigid needle shield (RNS) covering delivery member of the medicament delivery device, and wherein, during removal of the removable cap from the medicament delivery device, the RNS is removed from the medicament delivery device.

5. The medicament delivery device of claim 4, further comprising an RNS remover, wherein the RNS remover comprises a first engagement feature for coupling to the removable cap and a second engagement feature for coupling to the RNS.

6. The medicament delivery device of claim 5, wherein the first engagement feature is a snap-fit feature, and wherein the second engagement feature is a prong.

7. The medicament delivery device of claim 1, wherein the medicament delivery device is an automatic injection device.

8. The medicament delivery device of claim 1, further comprising a window in the main body.

9. The medicament delivery device of claim 1, wherein the delivery member comprises a needle, and wherein the needle is axially fixed with respect to the syringe.

10. The medicament delivery device of claim 1, wherein the delivery member shield unit and the removable cap are axially locked with respect to the main body in a first state, and wherein the delivery member shield unit and the removable cap are unlocked and are axially moveable with respect to the main body in a second state.

11. The medicament delivery device of claim 1, wherein the delivery member shield unit comprises a delivery member cover.

12. The medicament delivery device of claim 11, wherein the delivery member cover extends distally and locks in an extended position after delivery of the medicament.

13. The medicament delivery device of claim 11, further comprising a delivery member shield link coupled to the delivery member cover.

14. The medicament delivery device of claim 1, wherein the removable cap includes one or more projections configured to interact with an inner surface of the main body when the device is in a locked configuration.

15. The medicament delivery device of claim 1, further comprising:

a tubular member arranged inside the delivery member shield unit, where the tubular member comprises a track and is coupled to the plunger rod, wherein the delivery member shield unit comprises a pin configured to interact with the track of the tubular member, and wherein, during removal of the removable cap, the pin on the delivery member shield unit travels in the track on the tubular member so as to cause rotation of the tubular member that releases the plunger rod thereby allowing the plunger rod to travel a predetermined distance so as to automatically prime the medicament delivery device.

16

16. The medicament delivery device of claim 15, wherein the tubular member comprises a first rib and a second rib, and wherein the predetermined distance is a distance between the first rib and the second rib.

17. The medicament delivery device of claim 16, wherein the plunger rod comprises a protrusion configured to interact with the first rib, and wherein the rotation of the tubular member moves the protrusion on the plunger rod off of the first rib.

18. The medicament delivery device of claim 17, further comprising a spring configured to, after the rotation of the tubular member moves the protrusion on the plunger rod off of the first rib, move the plunger rod in a distal direction until the protrusion interacts with the second rib.

19. The medicament delivery device of claim 18, wherein the syringe comprises a stopper, and wherein movement of the plunger rod in the distal direction causes the plunger rod to act on the stopper so as to prime the medicament delivery device.

20. The medicament delivery device of claim 15, wherein priming the medicament delivery device comprises expelling a priming portion of the medicament from the medicament delivery device, and wherein the priming portion of the medicament is between 0.05 ml and 0.2 ml.

* * * * *